(12) United States Patent
Begue et al.

(10) Patent No.: US 7,417,155 B2
(45) Date of Patent: Aug. 26, 2008

(54) ARTEMISININE DERIVATIVES, AND USES THEREOF FOR TREATING MALARIA

(75) Inventors: Jean-Pierre Begue, Paris (FR); Danièle Bonnet-Delpon, Paris (FR); Benoît Crousse, Verrieres le Buisson (FR); Michèle Ourevitch, Creteil (FR); Fatima Chorki, Linas (FR); Fabienne Grellepois, Chatenay-Malabry (FR); Guillaume Magueur, Le Plessis-Robinson (FR)

(73) Assignee: Centre National de la Recherche Scientifique, Paris (FR)

( * ) Notice: Subject to any disclaimer, the term of this patent is extended or adjusted under 35 U.S.C. 154(b) by 484 days.

(21) Appl. No.: 10/493,576

(22) PCT Filed: Oct. 25, 2002

(86) PCT No.: PCT/FR02/03675

§ 371 (c)(1), (2), (4) Date: Oct. 5, 2004

(87) PCT Pub. No.: WO03/035651

PCT Pub. Date: May 1, 2003

(65) Prior Publication Data

US 2005/0038024 A1 Feb. 17, 2005

(30) Foreign Application Priority Data

Oct. 26, 2001 (FR) .................................. 01 13869

(51) Int. Cl.
C07D 493/18 (2006.01)

(52) U.S. Cl. ........................ 549/348; 549/354; 514/450

(58) Field of Classification Search ................ 549/348, 549/354; 514/450
See application file for complete search history.

(56) References Cited

OTHER PUBLICATIONS

Ziffer et al. Journal of Medicinal chemistry, 1995, 38, 4120-4124 (p. 4121, compound 1).*

Yu Ming Pu et al., "Synthesis and Antimalarial Activities of Several Fluorinated Artemisinn Derivatives", Journal Medicinal Chemistry, American Chemical Society, Washington, DC 1995, vol. 38, pp. 4120-4124.

Truong Thi Thanh Nga et al., "Synthesis and Antimalarial Activities of Fluoroalkyl Derivatives of Dihydroartemisinin", Journal of Medicinal Chemistry, American Chemical Society, Washington, DC,vol. 41, 1998, pp. 4101-4108.

Ahmed Abouabdellah et al., "Synthesis and in vivo Antimalarial Activity of 12α-Trifluoromethyl-Hydroartemisinin", Bioorganic & Medicinal Chemistry Letters, Oxford, GB, vol. 6, No. 22, Nov. 19, 1996, pp. 2717-2720.

* cited by examiner

Primary Examiner—D. Margaret Seaman
Assistant Examiner—Nizal S Chandrakumar
(74) Attorney, Agent, or Firm—Young & Thompson

(57) ABSTRACT

A new artemisinin derivatives, of following general formula (I):

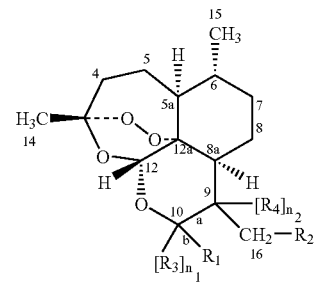

In which:
a and b represent a single or a double bond,
n1 and n2 represent 0 or 1,
$R_1$ represents a fluoroalkyl group or a fluoroaryl group,
$R_2$ represents a hydrogen atom, or a halogen atom, or a group, if appropriate ionisable, making it possible to render said compounds of formula (I) water-soluble,
$R_3$ represents a group, if appropriate ionisable, making it possible to render said compounds of formula (I) water-soluble,
$R_4$ represents H or OH. The invention also relates to the process by which they are obtained, and their uses in pharmaceutical compositions intended for the treatment of malaria.

9 Claims, No Drawings

ARTEMISININE DERIVATIVES, AND USES THEREOF FOR TREATING MALARIA

A subject of the present invention is new derivatives of artemisinin, a process for obtaining them, and their uses in pharmaceutical compositions intended for the treatment of malaria.

The rapid development of the phenomenon of resistance to anti-malarial drugs is particularly alarming because of its considerable consequences in Africa and South-East Asia. New medicaments must urgently be discovered for the treatment of malaria from multi-drug resistant *Plasmodium falciparum*.

In addition to the current need for effective malarial therapies, are added the mandatory costs linked with the localization of the epidemic in poorer countries. Artemisinin is a natural, inexpensive compound, extracted from a plant *Artemisia annua*, used in traditional Chinese medicine against malaria.

Artemisinin (ART) has appeared to be a promising medicament against these resistant strains; its effectiveness is however limited by a very short plasmatic half-life, and low activity by oral route.

By taking into account the specific properties provided by the presence of fluorinated groups (Rf), the Inventors have conceived and prepared fluorinated analogues of dihydroartemisinin (DHA) by hemisynthesis, by introducing a fluoroalkyl group on the strategic C-10 carbon, in order to slow down the various processes of the metabolism (oxidation, hydrolysis and glucuronidation) which take place on this site and thus to prolong the duration of the action of the compounds (Truong Thi Thanh Nga et al., 1998, J. Med. Chem., 41, 4101-4108). These fluoro artemisinins (F-ART) are more active than artemisinin and artesunate in vivo in mice. The survival rate is 100%. The preliminary results of pharmacokinetic studies seem to validate the hypothesis on the extension of the plasmatic half-life of an artemisinin derivative by the introduction of a fluorinated substituent on the C-10 site.

The problem of the insolubility in water of these compounds which limits the effectiveness of administration by oral route remains to be solved. A new generation of fluorinated derivatives of artemisinin had to be envisaged and synthesis found allowing the presence of a fluoroalkyl group in C-10 and the introduction of a function, which is if appropriate ionisable (amine, acid etc.), making it possible to render these compounds water-soluble.

The present invention follows on from the highlighting by the Inventors, that it is possible to prepare new artemisinin derivatives, substituted both by a fluoroalkyl group in C-10, which has proved to extend the period of action of artemisinin, and by a function, if appropriate ionisable, on the carbon in position 10 or 16, which allows solubility in water and therefore easy administration by oral route.

The present invention has consisted of finding a chemical means of introducing an ionisable function on artemisinin derivatives fluorinated in C-10. Difficulties in synthesis have resided in the following facts: i) The starting products have few anchorage points allowing the introduction of new functions without harming activity; ii) The presence of fluorine in the molecules considerably alters its chemical reactivity.

The inventors have been able to resolve the problem, by preparing allylic bromide in C-9, a key product which allows the introduction of any other function, and thus by using inexpensive chemical reagents. Compounds which are water-soluble allow administration by oral route, which facilitates the treatment of malaria.

The invention relates to compounds of following general formula (I):

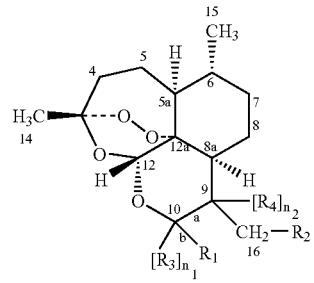

(I)

In which:

a and b represent a single or a double bond, provided that a and b can not both represent a double bond, n1 and n2, independently from one another, represent 0 or 1, provided that when a represents a double bond then n1=n2=0 and when b represents a double bond then n1=0, $R_1$ represents:
A fluoroalkyl group of approximately 1 to approximately 5 carbon atoms, and comprising at least two fluorine atoms, such as the following perfluoroalkyl groups: $CF_3$, $C_2F_5$, $C_3F_7$, $C_4F_9$, and $C_5F_{11}$, Or a fluoroaryl group comprising at least two fluorine atoms, such as the $C_6F_5$ perfluoroaryl group, Or a $CF_2$ group when b represents a double bond and n1=0, $R_2$ represents a hydrogen atom, or a halogen atom, such as Br, or a group, if appropriate ionisable, making it possible to render said compounds of formula (I) water-soluble, such as the groups derived from piperazine, morpholine, alkylamine, alkoxy, ester or diester, acid or diacid, thioalkyl, alkylhydroxyl, or glycosyl, $R_3$ represents a group, if appropriate ionisable, making it possible to render said compounds of formula (I) water-soluble, such as:

An OR group in which R represents H, or an alkyl group of approximately 1 to 10 carbon atoms, if appropriate substituted, in particular a group of formula $—CH_2)_n$—$R_5$ in which n represents an integer from 1 to 5, and $R_5$ represents: $CF_3$, OH, $—CH=CH_2$, COOH, COH, CHOH—$CH_2OH$, or a phenyl group, if appropriate substituted, in particular by $CH_2OH$, $NH_2$, or a NH—$R_6$ group in which $R_6$ represents an alkyl or alkoxy group of 1 to 5 carbon atoms, or an arylalkyl or arylalkoxy group, such as the —NH—$C_6H_5$—$OCH_3$, $R_4$ represents H or OH.

A more particular subject of the invention is compounds of general formula (Ia) corresponding to abovementioned formula (I) in which a represents a double bond, b represents a single bond, and n1=n2=0, namely compounds of following formula:

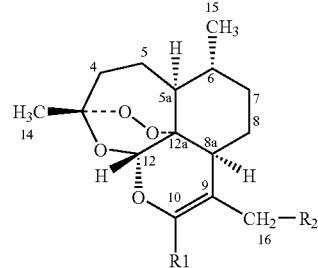

(Ia)

In which:
R₁ represents:
  A fluoroalkyl group of approximately 1 to approximately 5 carbon atoms, and comprising at least two fluorine atoms, such as the following perfluoroalkyl groups: $CF_3$, $C_2F_5$, $C_3F_7$, $C_4F_9$, and $C_5F_{11}$,
  Or a fluoroaryl group comprising at least two fluorine atoms, such as the perfluoroaryl group $C_6F_5$,
R₂ represents a halogen atom, such as Br, or a group, if appropriate ionisable, making it possible to render said compounds of formula (I) water-soluble, such as the groups derived from piperazine, morpholine, alkylamine, alkoxy, ester or diester, acid or diacid, thioalkyl, alkylhydroxyl, or glycosyl, A subject of the invention is also the compounds of formula (Ia-bis), corresponding to the abovementioned compounds of formula (I) in which R₂ represents a group, if appropriate ionisable, making it possible to render said compounds water-soluble.

A more particular subject of the invention is the compounds of formula (Ia-bis) in which R₂ represents:
  A group derived from piperazine, if appropriate substituted by an amine, alcohol, or acid function, such as the piperazine ethanol group of formula,

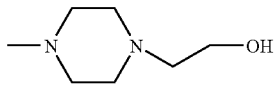

Or a morpholino group of formula,

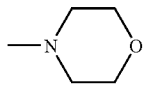

Or an alkylamine group of approximately 1 to approximately 10 carbon atoms, if appropriate substituted by a hydroxyl, such as the ethylamine group of formula —NH—CH₂—CH₃, or the —NH—CH₂—CH₂—OH group,
  Or an alkoxy group of approximately 1 to approximately 10 carbon atoms, if appropriate substituted by a hydroxyl or amine function, such as the ethoxy group of formula —O—CH₂—CH₃, the —O—CH₂—CH₂—OH group, or the —O—CH₂—CH₂—NHR group in which R represents an alkyl group of 1 to 5 carbon atoms,
  Or an alkyl group of approximately 1 to approximately 10 carbon atoms, substituted by one or more —COOR functions in which R represents H or an alkyl, alkylamine, or alkylhydroxy group, of approximately 1 to approximately 4 carbon atoms, such as the group of formula

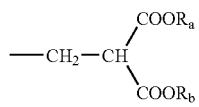

in which $R_a$ and $R_b$ represent H or CH₃,
  or a thioalkyl group of approximately 1 to approximately 6 carbon atoms, such as the group of formula —S—CH₂—CH₃,
  or an alkylhydroxyl group of approximately 1 to approximately 10 carbon atoms,
  or a glycosyl group such as glucuronic acid or other nonasaccharides.

The invention more particularly relates to the abovementioned compounds, of formula (I) or (Ia) in which R₁ represents $CF_3$, $C_2F_5$, $C_3F_7$, or $C_6F_5$.

A more particular subject of the invention is the abovementioned compounds of formula (Ia), corresponding to the following formulae:

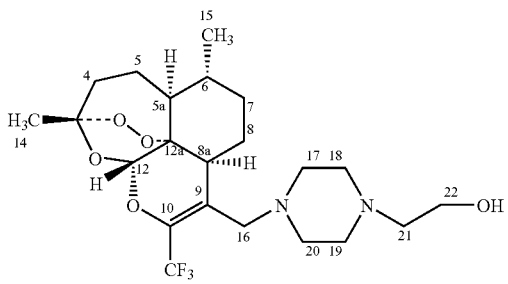

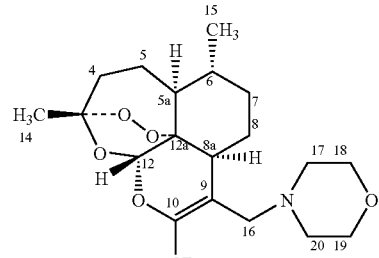

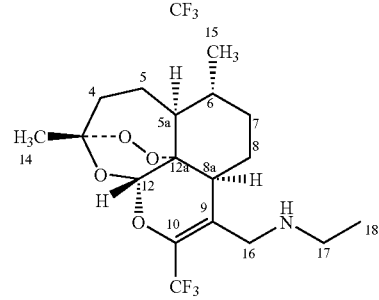

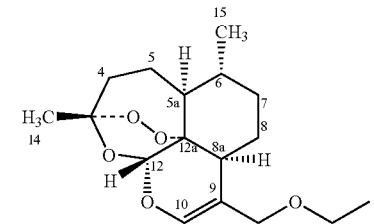

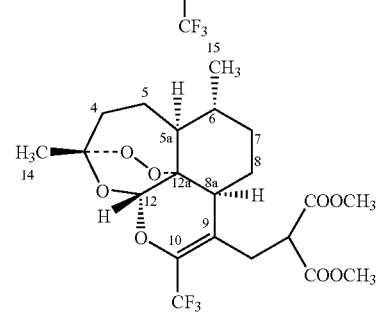

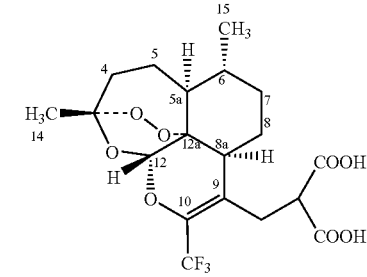

-continued

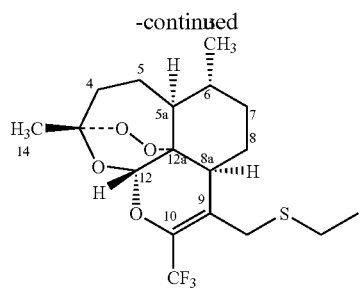

The invention also relates to compounds, of general formula (Ib) corresponding to formula (I) in which a and b represent a single bond, and n1=n2=1, namely compounds of following formula:

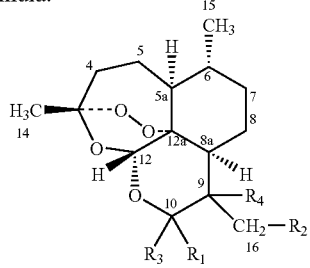

In which:
$R_1$ represents:
- A fluoroalkyl group of approximately 1 to approximately 5 carbon atoms, and comprising at least two fluorine atoms, such as the following perfluoroalkyl groups: $CF_3$, $C_2F_5$, $C_3F_7$, $C_4F_9$, and $C_5F_{11}$,
- Or a fluoroaryl group comprising at least two fluorine atoms, such as the perfluoroaryl group $C_6F_5$, $R_2$ represents a hydrogen atom, or a halogen atom, such as Br, or a group, if appropriate ionisable, making it possible to render said compounds of formula (I) water-soluble, such as the groups derived from piperazine, morpholine, alkylamine, alkoxy, ester or diester, acid or diacid, thioalkyl, alkylhydroxyl, or glycosyl, $R_3$ represents:
- An OR group in which R represents H, or an alkyl group of approximately 1 to 10 carbon atoms, if appropriate substituted, in particular a group of formula —$(CH_2)_n$—$R_5$ in which n represents an integer from 1 to 5, and $R_5$ represents: $CF_3$, OH, —CH=$CH_2$, COOH, COH, CHOH—$CH_2OH$, or a phenyl group, if appropriate substituted, in particular by $CH_2OH$,
- $NH_2$, or a NH—$R_6$ group in which $R_6$ represents an alkyl or alkoxy group of 1 to 5 carbon atoms, or an arylalkyl or arylalkoxy group, such as the —NH—$C_6H_5$—$OCH_3$, $R_4$ represents H or OH.

A more particular subject of the invention is compounds of above-mentioned general formula (Ib) in which $R_1$ represents $CF_3$, $R_2$ and $R_4$ represent a hydrogen atom, and $R_3$ is such as defined above, namely compounds of following formula:

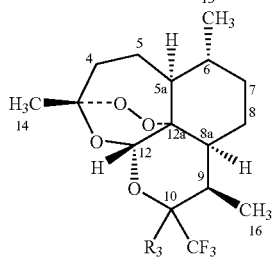

The invention more particularly relates to compounds of abovementioned formula (Ib), corresponding to following formulae:

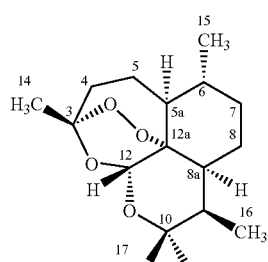

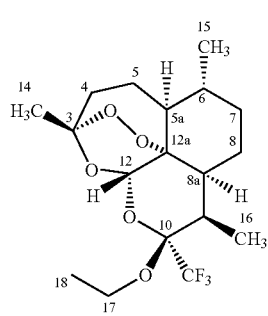

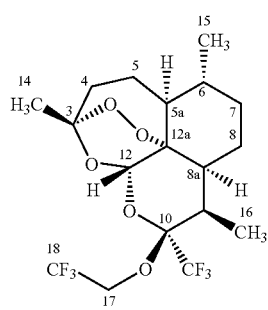

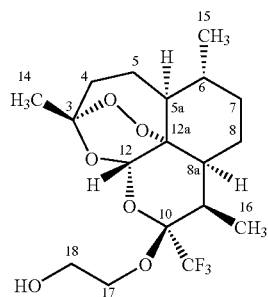

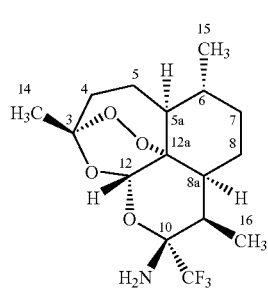

-continued

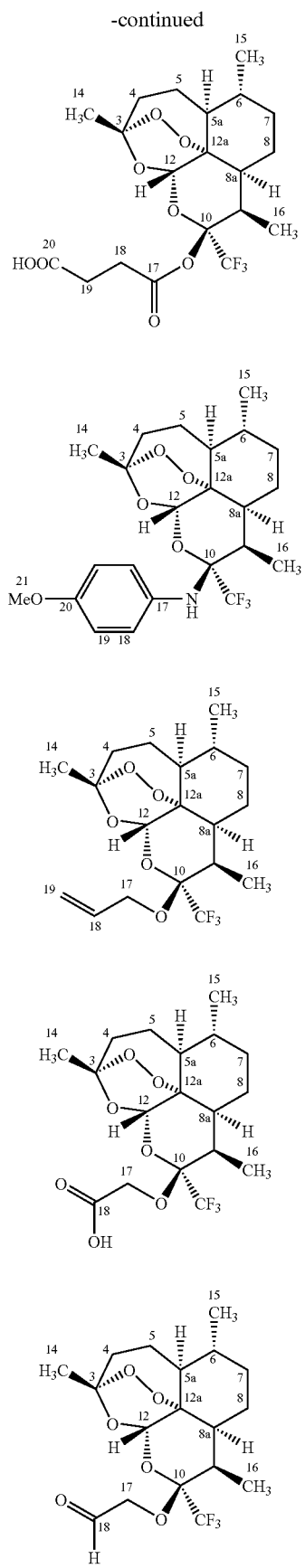

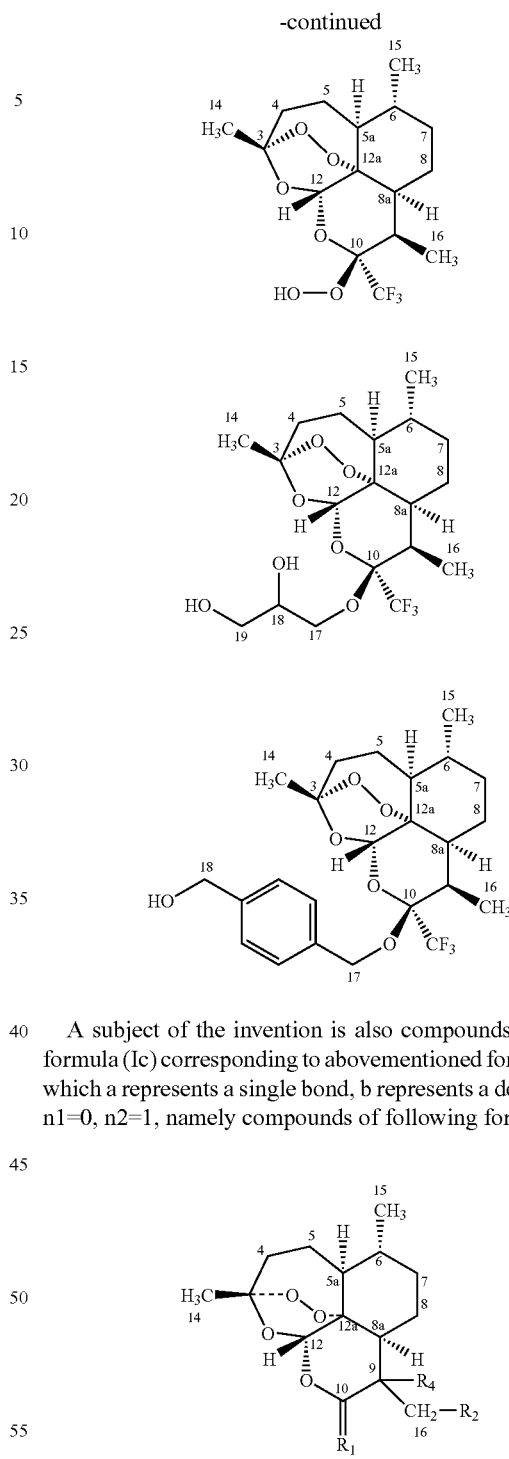

A subject of the invention is also compounds of general formula (Ic) corresponding to abovementioned formula (I), in which a represents a single bond, b represents a double bond, n1=0, n2=1, namely compounds of following formula:

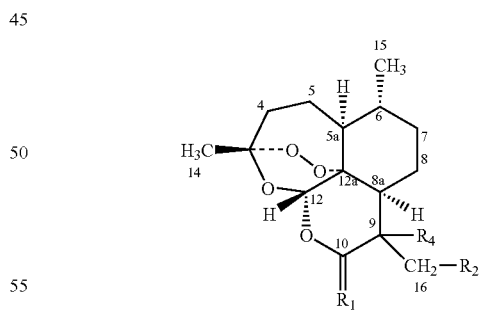

In which:

R₁ represents a CF₂ group,

R₂ represents a hydrogen atom, or a halogen atom, such as Br, or a group, if appropriate ionisable, making it possible to render said compounds of formula (I) water-soluble, such as the groups derived from piperazine, morpholine, alkylamine, alkoxy, ester or diester, acid or diacid, thioalkyl, alkylhydroxyl, or glycosyl, R₄ represents H or OH.

A more particular subject of the invention is the compound of above-mentioned formula (Ic), of following formula:

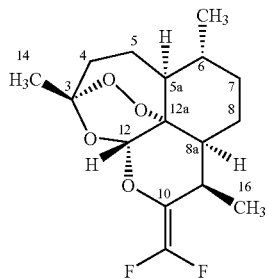

The invention also relates to any pharmaceutical composition characterized in that it comprises at least one compound of formula (Ia) defined above, and more particularly of formulae (Ia-bis), (Ib), and (Ic), combined with a pharmaceutically acceptable vehicle.

The pharmaceutical compositions of the invention are advantageously presented in a form intended for administration by oral, injectable, or rectal route.

Preferably, the pharmaceutical compositions of the invention are characterized in that the unit dose of compounds of formula (I) as active ingredient of said compositions, is approximately 5 mg, to approximately 5 g, for a dosage of approximately 1 mg/kg/day to approximately 100 mg/kg/day.

The invention also relates to any pharmaceutical composition as defined above, characterized in that it also comprises one or more other anti-malarial compounds chosen in particular from pyrimethamine, sulfadoxine, quinine, lumefantrine, mefloquine.

A subject of the invention is also the use of a compound of formula (I) defined above, and more particularly of abovementioned formulae (Ia-bis), (Ib), and (Ic), for the preparation of a medicament intended for the treatment of malaria, and more particularly malaria caused by strains of *Plasmodium falciparum* resistant to chloroquine.

The invention also relates to the products comprising:
At least one compound of formula (I) defined above, and more particularly of abovementioned formulae (Ia-bis), (Ib), and (Ic),
And at least one other anti-malarial compound chosen in particular from those listed above, as a combined preparation for simultaneous, separate or sequential use in the treatment of malaria.

The invention also relates to a process for the preparation of compounds of formula (Ia) defined above, characterized in that it comprises the following stages:
Treatment of artemisinin with a fluoroalkylating or fluoroarylating agent as defined above in the scope of the definition of $R_1$, such as a trimethylsilane in the presence of fluoride ions, or an organolithium, which leads to the obtaining of the compound of the following formula:

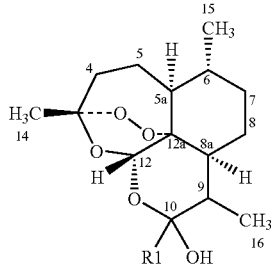

In which $R_1$ is as defined above,
Dehydration of the compound obtained in the previous stage, in particular by treatment with $SOCl_2$ in pyridine, which leads to the obtaining of the following compound of formula (I):

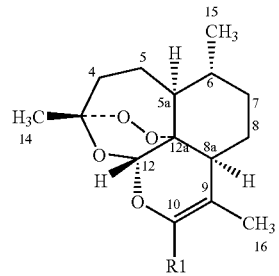

In which $R_1$ is as defined above,
Treatment of the compound obtained in the previous stage with a halogen, such as bromine, which leads to the obtaining of the following compound of formula (Ia):

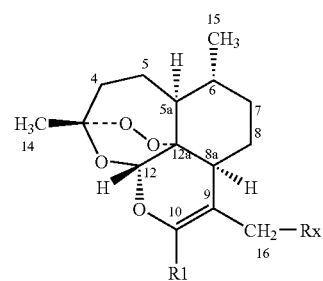

In which $R_x$ represents a halogen atom, and $R_1$ is as defined above,
Substitution of the $R_x$ halogen by a group, if appropriate ionisable, allowing solubility in water as defined above, which leads to the obtaining of a compound of the following formula (Ia-bis):

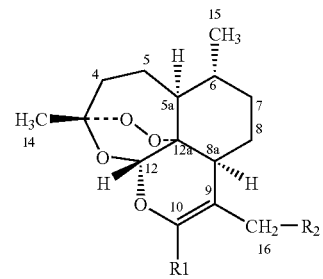

In which $R_1$ and $R_2$ are as defined above.
The invention also relates to the compounds used as synthesis intermediates within the scope of the abovementioned preparation process, and corresponding to the following formulae:

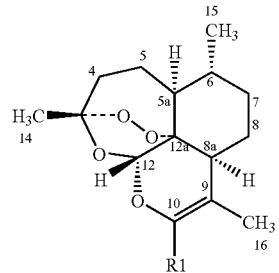

In which $R_1$ is as defined above,

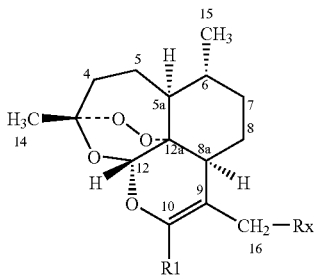

In which $R_x$ represents a halogen atom, and $R_1$ is as defined above.

A subject of the invention is also a process for the preparation of compounds of formulae (Ib) and (Ic), characterized in that it comprises the treatment of the compound of following formula:

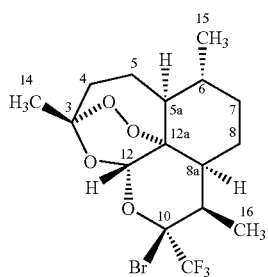

With the nucleophile of formula HO—R, in which R is as defined above, in the case where one wishes to obtain a compound of formula (Ib) in which $R_3$ represents OR, or with acetonitrile in the case where one wishes to obtain a compound of formula (Ib) in which $R_3$ represents $NH_2$, or with $NH_2$—$R_6$ in which $R_6$ is as defined above, in the case where one wishes to obtain a compound of formula (Ib) in which $R_3$ represents —$NHR_6$, agitation at room temperature, followed by treatment of the reaction mixture with an aqueous solution of sodium bicarbonate, drying, in particular over magnesium sulphate, and solvent evaporation, which leads to the obtaining of the compound of following formula (Ib):

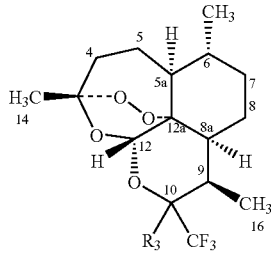

In which $R_3$ is as defined above,

With methyllithium at 78° C. under agitation, then at room temperature, followed by hydrolysis, which leads to the obtaining of compound of following formula (Ic):

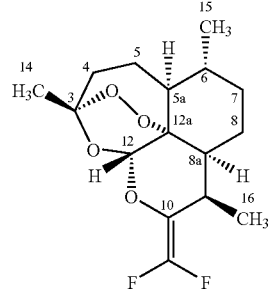

The invention will be further illustrated using the detailed description of new artemisinin derivatives, and their properties.

I Compounds of Formula (Ia)

The compounds of formula (Ia) are prepared from 10-$CF_3$ hydroartemisinin, already described by the Inventors (Truong Thi Thanh Nga et al., 1998, mentioned above), which has the following formula:

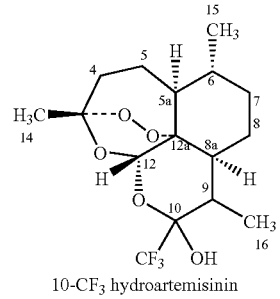

10-$CF_3$ hydroartemisinin

The latter is dehydrated and the enol ether obtained reacts with $Br_2$ in order to produce an allylic bromide which is the key intermediate being able to be substituted by various functions.

Preparation of methyl-9, $CF_3$-10 hydroartemisinin

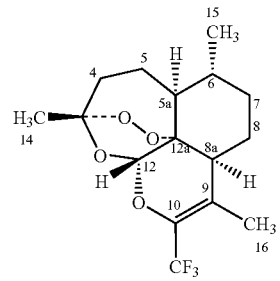

Hemiketal (100 mg, $2.8 \times 10^{-4}$ mol) dissolved in pyridine (1 ml) (distilled and stored on KOH) is introduced into a flask under argon. $SOCl_2$ (1.5 eq, 0.032 ml) is added dropwise at 0° C. The reaction mixture is agitated for 1 hour. A solution of 3N hydrochloric acid HCl is added (5 ml), and extraction is carried out with dichloromethane. The organic solution is washed with a sodium chloride saturated solution and dried over $MgSO_4$. Olefin is obtained in a mixture with the chlorinated derivative in a 90/10 ratio. Silica gel chromatography (petrol ether/ethyl acetate: 95/5) leads to pure olefin in the form of white crystals (82 mg, 78%).

$^{19}F$ NMR δ (ppm) $-65.2$ (qd, $^5J_{FH}=2.5$ Hz, $^6J_{FH}=1.5$ Hz, 3 F, $CF_3$)

$^1H$ (ppm) 1.01 (d, $^3J_{H15-H6}$, 3 H, $H_{15}$), 1.18 (m, 1 H, $H_{7ax}$), 1.24 (qd, $^2J=^3J_{H8ax-H7ax}=^3J_{H8ax-H8a}=13$ Hz, $^3J_{H8ax-H7eq}=3$ Hz 1 H, $H_{8ax}$), 1.44 (s, 3 H, $H_{14}$ and m, 1 H, $H_{5a}$), 1.45 (m, 1 H, $H_5$), 1.46 (m, 1 H, $H_6$)1.73 (dq, $^2J=13$ Hz, $^3J_{H7eq-H6ax}=^3J_{H7eq-H8eq}=3J_{H7eq-H8ax}=3$ Hz, 1 H, $H_{7eq}$), 1.82 (m, 1 H, $H_{8a}$), 1.83 (q, $^5J_{HF}=2.5$ Hz, 3 H, $H_{16}$), 1.95 (m, 1 H, $H_5$), 2.03 (m, 1 H, $H_{5eq}$), 2.05 (ddd, $^2J=14.5$ Hz, $^3J_{H4eq-H5ax}=3$ Hz, $^3J_{H4eq-H5eq}=4.5$ Hz, 1 H, $H_{4eq}$), 2.41 (ddd, $^2J=14.5$ Hz, $^3J_{H4ax-H5ax}=13$ Hz, $^3J_{H4ax-H5eq}=4$ Hz, 1 H, $H_{4ax}$), 5.7 (s, 1 H, $H_{12}$).

$^{13}C$ δ (ppm) 15.5 ($C_{16}$), 20.2 ($C_{15}$), 24.5 ($C_5$), 25.7 ($C_{14}$), 28.9 ($C_8$), 34.2 ($C_7$), 36.2 ($C_4$), 37.7 ($C_6$), 47.5 ($C_{8a}$), 50.8 ($C_{5a}$), 78.5 ($C_{12a}$), 90.5 ($C_{12}$), 105.0 ($C_3$), 112.1 (m, $C_9$), 135 (m, $C_{10}$).

MP=118° C. (EP/AcOEt)

$[α]_D=-42.6°$ (c=0.54, MeOH)

| Elementary analysis C$_{16}$H$_{23}$F$_3$O$_4$ | | | |
|---|---|---|---|
| % Calculated | C | 57.14 | 6.89 |
| % Found | H | 57.46 | 6.33 |

Preparation of allylic bromide

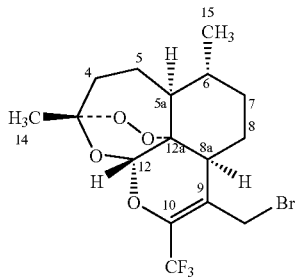

Olefin (100 mg, 3 10$^{-4}$ mol) dissolved in 5 ml of carbon tetrachloride CCl$_4$ is introduced into a flask under argon at 0° C. A solution of dibromine in carbon tetrachloride (5%, 0.4 ml) is added dropwise. The reaction medium is agitated for approximately 2 hours. After washing with a solution of 38% sodium hydrogen-sulphite and extraction with diethyl ether, the solvent is evaporated, then the residue is purified by chromatography on a silica column (petrol ether/ethyl acetate: 90/10) in order to produce allylic bromide in the form of pale yellow crystals (105 mg, 88%).

$^{19}$F δ (ppm) −65.8 (s, 3F, CF$_3$)

$^1$H δ (ppm) 0.99 (d, $^3J_{H15-H6}$=6 Hz, 1 H, H$_{15}$), 1.16 (ddd, $^3J_{H7axH7eq}$=13.5 Hz, $^3J_{H7axH8ax}$=11.5 Hz, $^3J_{H7axH8eq}$=3.5 Hz, 1 H, H$_{7ax}$), 1.3 (qd, $^2$J=$^3J_{H8axH7ax}$=$^3J_{H8axH8a}$=13.5 Hz, $^3J_{H8axH7eq}$=3.5 Hz, 1 H, H$_{8ax}$), 1.4 (m, 1 H, H$_6$), 1.41 (s, 1 H, H$_{16}$), 1.5 (m, 2 H, H$_5$ and H$_{5a}$), 1.72 (dq, $^2$J=13 Hz, $^3J_{H7eqH8ax}$=$^3J_{H7eqH8eq}$=$^3J_{H7eqH6}$=3.5 Hz, 1 H, H$_{7eq}$), 1.96 (m, 1 H, H$_5$), 2.04 (ddd, $^2$J=15 Hz, $^3J_{H4eqH5ax}$=4.5 Hz, J$_{H4eqH5eq}$=3 Hz, 1 H, H$_{4eq}$) 2.11 (dtd, $^2$J=13.5 Hz, $^3J_{H8eqH7eq}$=$^3J_{H8eqH7ax}$=3.5 Hz, $^3J_{H8eq}$H$_{8a}$=4.5 Hz, 1 H, H$_{8eq}$), 2.19 (ddd, $^3J_{H8aH8\ ax}$=12.5 Hz, $^3J_{H8aH8eq}$=4.4 Hz, $^4J_{CF3H8}$=1.5 Hz, 1 H, H$_{8a}$), 2.4 (td, $^2J_{H4axH5ax}$=$^3$JH$_{4ax}$H$_{5ax}$=13.5 Hz, $^3J_{H4axH5eq}$=4 Hz, 1 H, H$_{4ax}$), 4.0 (dq, $^2J_{HaHb}$=11 Hz, $^5J_{HaCF3}$=1.5 Hz 1 H, H$_a$), 4.28 (dq, $^2$J=11 Hz, $^5J_{HbCF3}$=1 Hz, 1 H, H$_b$), 5.7 (s, 1 H, H$_{12}$).

$^{13}$C δ (ppm) 20 (C$_{15}$), 24.2 (C$_5$), 25.5 (C$_{14}$), 29. (CH$_2$Br and C$_8$), 34 (C$_7$), 36 (C$_4$), 37.5 (C$_6$), 44.0 (C$_{8a}$), 50.5 (C$_{5a}$), 77(C$_{12a}$), 91 (C$_{12}$), 105 (C$_3$), 112 (C$_9$), 139 (C$_{10}$).

MP=119.5° C. (EP/Et$_2$O).

| Elementary analysis C$_{16}$H$_{22}$O$_4$ F$_3$Br | | |
|---|---|---|
| % Calculated | C, 46.28 | H, 5.34 |
| % Found | C, 46.17 | H, 5.10 |

Substitution by piperazine ethanol

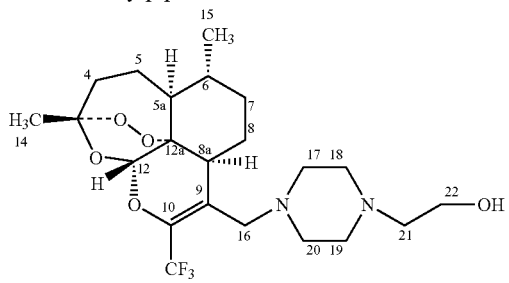

Allylic bromide (100 mg, 2.4 10$^{-4}$ mol) in 8 ml of THF is introduced into a flask under argon and at 0° C., then piperazine ethanol is added dropwise (126 mg, 2 eq). The mixture is agitated whilst allowing the temperature to rise. The evolution of the reaction is followed by CCM. After 5 hours, the medium is taken up with a sodium chloride saturated solution. The aqueous phase is extracted with Et$_2$O (3×10 ml), then the organic phase is dried over MgSO$_4$ and the compound (110 mg) is obtained in the form of light brown crystals with a yield of 98% and with >95% purity. The compound is recrystallized in a petrol ether/AcOEt mixture.

NMR $^{19}$F δ (ppm) −63.1(s, 3F, CF$_3$)

$^1$H δ (ppm) 0.97 (d, $^3J_{H15H6}$=5.5 Hz, 3 H, H$_{15}$), 1.4 (s, 3 H, H$_{14}$), 1.98 (td, $^3J_{H4axH5ax}$=$^2$J=13.5 Hz, $^3J_{H4axH5eq}$=3.5 Hz, 1 H, H$_{4ax}$), 2.51 (m, 8 H), 2.84 (s br, 1 HOH), 3.05 (s br, 2 H), 3.58 (t, $^3J_{H22H21}$=5.5 Hz, 2 H, H$_{22}$), 5.69 (s, 1 H, H$_{12}$).

$^{13}$C δ (ppm) 20.1 (C$_{15}$); 24.4 (C$_5$); 25.5 (C$_{14}$); 28.7 (C$_8$); 33.9 (C$_7$); 36.0 (C$_4$); 37.5 (C$_6$); 42.0 (C$_{8a}$); 42.9 (C$_{16}$), 50.3 (C$_{5a}$); 52.5, 54.1, 57.7, 59.2, 77.9 (C$_{12a}$); 90.8 (C$_{12}$); 104.9 (C$_3$); 113.5 (C$_9$); 138 (C$_{10}$), CF$_3$ not observed.

Melting point (EP/AcOEt)=126° C.

| Elementary analysis C$_{22}$ H$_{35}$ O$_5$ F$_3$ N$_2$ | | |
|---|---|---|
| % Calculated | C, 56.88 | H, 7.59 | N, 6.03 |
| % Found | C, 56.08 | H, 7.21 | N, 5.27 |

Hydrochloride:

Melting point: 158° C.

Solubility in water greater than 50 mg/ml

NMR $^{19}$F δ (ppm) −63.1(s, 3F, CF$_3$)

Substitution by morpholine

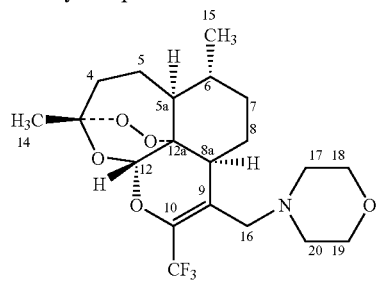

Morpholine (126 mg, 2 eq) is added dropwise, under argon, at 0° C., to a solution of allylic bromide (500 mg, 0.1 mmol) in THF (50 mL). The reaction mixture is agitated whilst allowing the temperature to rise. The evolution of the reaction is followed by CCM. After 7 hours, the reaction medium is hydrolysed with a NaCl saturated solution. After extraction with Et$_2$O (3×20 mL), the organic phase is then dried over MgSO$_4$. After evaporation of the solvent, the compound is purified by silica gel chromatography (EP/AcOEt: 30/70) so as to produce an orange brown solid with morpholine (400 mg, 79%).

$^{19}$F δ (ppm) −63.0 (s, 3 F, CF$_3$)

$^1$H δ (ppm) 0.98 (d, $^3J_{H15-H6}$=5.5 Hz, 3 H, CH$_3$-15), 1.4 (s, 3 H, CH$_3$-14), 2.3 (m, 2 H), 2.5 (m, 6 H), 3.04 (m, $^3J_{Ha-Hb}$=13.5 Hz, $^5J_{CH2-CF3}$=2 Hz, 2 H), 3.65 (m, 4 H), 5.7 (s, 1 H, H-12).

$^{13}$C δ (ppm) 20.0 (C-15), 24.3 (C-5), 25.4 (C-14), 28.6 (C-8), 33.9 (C$_7$), 37.5 (C-4 and C-6), 41.9 (C-8a), 42.9 (C-16), 53.0, 54.4, 67.1, 50.3 (C-5a), 77.8 (C-12a), 90.8 (C-12), 104.8 (C-3), 113.1 (C-9), 137.6 (q, $^2J_{C-F}$=34 Hz, C-10), CF$_3$ not observed.

[α]$^{33}_D$=+67.4 (c=0.9, MeOH).

| Elementary analysis C$_{20}$H$_{30}$O$_5$ F$_3$ N | | | |
|---|---|---|---|
| % Calculated | C, 56.99 | H, 7.17 | N, 3.32 |
| % Found | C, 55.42 | H, 6.72 | N, 3.09 |

Hydrochloride:
Melting point: 110° C.
Solubility in water greater than 20 mg/ml
$^{19}$F δ (ppm) −63.0 (s, 3 F, CF$_3$)
Substitution by ethylamine

[Chemical structure diagram]

A solution of 2 M ethylamine (0.36 mL, 3 eq) in THF is added slowly at 0° C. to a solution of allylic bromide (100 mg, 0.25 mmol) in THF (5 mL). The mixture is agitated whilst allowing the temperature to rise. The evolution of the reaction is followed by CCM. The solution is agitated for 8 hours then hydrolyzed with a sodium chloride saturated solution. After extraction in Et$_2$O (4×5 mL), the organic phase is dried over MgSO$_4$. After evaporation of the solvent, the compound is purified by silica gel chromatography (EP/AcOEt: 50/50) so as to produce a yellow oil (64 mg, 68%).

$^{19}$F δ (ppm) −63.2 (s, 3F, CF$_3$)
$^1$H δ (ppm) 0.97 (d, $^3$J$_{H15-H6}$=5.5 Hz, 3 H, CH$_3$-15), 1.1 (t, $^3$J$_{CH3-CH2}$=7 Hz, 3 H, CH$_3$), 1.4 (s, 3 H, CH$_3$-14), 2.3 (m, 2 H), 3.25 (d, $^2$J$_{Ha-Hb}$=13.5 Hz, 1 H, Ha), 3.5 (d, $^2$J$_a$=13.5 Hz, Hb), 5.7 (s, 1 H, H-12).
$^{13}$C δ (ppm) 14.5 (C-18), 20.0 (C-15), 24.3 (C-5), 25.5 (C-14), 28.9 (C-8), 33.8 (C-7), 36 (C-4), 37.5 (C-6), 42.5 (C-16), 42.6 (C-8a), 43.0, 50.2 (C-5a), 77.8 (C-12a), 90.9 (C-12), 105.0 (C-3), 114.2 (C-9), C-10 and CF$_3$ not observed.
[α]$^{33}_D$=+55.6° (c=0.9, MeOH).

| Elementary analysis C$_{18}$H$_{28}$ O$_4$F$_3$N: | | | |
|---|---|---|---|
| % Theoretical | C, 56.98 | H, 7.43 | N, 3.69 |
| % Experimental | C, 55.25 | H, 6.81 | N, 2.99 |

$^{19}$F δ (ppm) −63.1 (s, 3 F, CF$_3$)
Substitution by ethanol FC 487

[Chemical structure diagram]

Allylic bromide (100 mg, 1 eq, 0.24 mmol) and 10% (4 mg) of KI are added at 0° C. to a solution of sodium ethylate in THF prepared under argon from ethanol (0.03 ml, 2 eq, 0.5 mmol) and NaH (2 eq, 20 mg) in 10 ml of THF. The mixture is agitated for approximately 17 hours at ambient temperature then hydrolysed with a NaCl saturated solution. After extraction with Et$_2$O, the organic phase is dried over MgSO$_4$. After evaporation of the solvent, the residue is purified by rapid filtration on silica gel (EP/AcOEt: 95/5) in order to produce a white solid (85 mg, 95%).

$^{19}$F δ (ppm) −64.06 ppm (s, 3F, CF$_3$)
$^1$H δ (ppm) 0.98 (d, $^3$J$_{H15-H6}$=5.5 Hz, 3 H, CH$_3$-15), 1.18 (t, $^3$J$_{CH3-CH2}$=7 Hz, 3H, CH$_3$), 1.4 (s, 3H, CH$_3$-14), 3.3 (qd, $^3$J$_{Ha_2CH3}$=7 Hz, $^2$J$_{Ha-Hb}$=9 Hz, 1 H, Ha), 3.5 (qd, $^3$J$_{Hb-CH3}$=7 Hz, $^2$J=9 Hz, 1 H, Hb), 4.1 (s, 2 H, CH$_2$), 5.7 (s, 1 H, H-12).
$^{13}$C δ (ppm) 15.1 (CH$_3$), 20.2 (C-15), 24.4 (C-5), 25.5 (C-14), 28.9 (C-8), 9 (C-7), 35.9 (C-4), 37.5 (C-6), 42.2 (C-8a), 50.4 (C-5a), 64.3 (OCH$_2$), 65.0 (C-16), 77.7 (C-12a), 90.9 (C-12), 104.9 (C-3), 113.1 (C-9), CF$_3$ and C-10 not observed.
Melting point (EP/Et$_2$O)=52° C.
α$^{33}_D$=+103.5° (c=0.8, MeOH).

| Elementary analysis C$_{18}$ H$_{27}$ O$_5$ F$_3$ | | |
|---|---|---|
| % Calculated | C, 56.83 | H, 7.15 |
| % Found | C, 56.97 | H, 6.98 |

Substitution by methyl malonate

[Chemical structure diagram]

Methyl malonate (0.36 ml, 1.5 eq, 3 mmol) and NaH (3 eq, 140 mg) are placed under argon in 8 ml of THF at 0° C. Allylic bromide (800 mg, 1 eq, 1.9 mmol) is then added. The mixture is agitated for 4 hours 30 minutes at ambient temperature then hydrolysed with an NaCl saturated solution. The aqueous phase is extracted with Et$_2$O, then the organic phase is dried over MgSO$_4$. After evaporation of the solvent, the compound is purified by silica gel chromatography (EP/AcOEt: 90/10) in order to produce a white solid (810 mg) with a yield of 90%.

$^{19}$F δ (ppm) −66.14 ppm (s, 3F, CF$_3$)
$^1$H δ (ppm) 0.94 (d, $^3$J$_{H15-H6}$=5.5 Hz, 3 H, CH$_3$-15), 1.35 (s, 3 H, CH$_3$-14), 2.5 (ddq, $^2$J$_{Hb-Ha}$=14.5 Hz, $^3$J$_{Hb-CH}$=6 Hz, $^5$J$_{Hb-CF3}$=2 Hz 1 H, Hb), 3.0 (ddq, $^2$J$_{Ha-Hb}$=14.5 Hz, $^3$J$_{Ha-CH}$=6 Hz, $^5$J$_{Ha-CF3}$=1.5 Hz, 1 H, Ha), 3.5 (dd, $^3$J$_{CH-Ha}$=$^3$J$_{CH-Hb}$=6 Hz, 1H, CH), 3.7 (s, 3 H, CH$_3$), 3.71 (s, 3 H, CH$_3$), 5.6 (s, 1 H, H-12).
$^{13}$C δ (ppm) 19.9 (C-15), 25.4 (CH$_2$), 25.5 (C-14), 28.7 (C-8), 33.9 (C-7), 35.9 (C-4), 37.5 (C-6), 42.1 (C-8a), 45.1 (CH), 50.2 (C-5a), 77.7 (C-12a), 90.5 (C-12), 104.8 (C-3), 112.3 (C-9), 136.8 (C-10), 168.9 (CO), 169.5 (CO), CF$_3$ not observed.
Melting point (EP/Et$_2$O)=84° C.
α$^{26}_D$=+70.7° (c=0.9, MeOH).

| Elementary analysis C$_{21}$ H$_{29}$ O$_8$ F$_3$ | | |
|---|---|---|
| % Calculated | C, 54.43 | H, 6.31 |
| % Found | C, 53.90 | H, 5.88 |

Hydrolysis to diacid

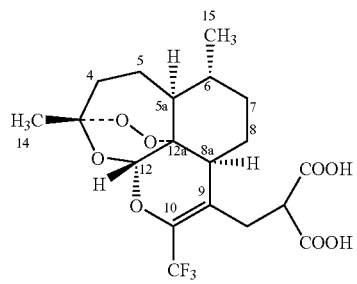

A solution of lithium hydroxide (17 mg, 3.3 eq, 0.7 mmol) in 1 mL of water is added to a solution of diester (100 mg, 0.2 mmol) in 1 mL of acetonitrile. The mixture is agitated for 5 hours at ambient temperature, then acidified with a solution of HCl until an acid pH is obtained. After extraction with an Et$_2$O/AcOEt mixture (2:1) and washing with a NaCl saturated solution, the organic phase is dried over MgSO$_4$. After evaporation of the solvent, the compound is purified by silica gel chromatography (EP/AcOEt: 30/70) in order to produce a slightly ecru foam (40 mg) with a yield of 40% (this diacid contains 8% of diester, it has not been purified).

$^{19}$F δ (ppm) −66.8 ppm (s, 3 F, CF$_3$)

$^1$H δ (ppm) 0.97 (d, $^3J_{H15-H6}$=4.5 Hz, 3H, H-15), 1.24 (s, 3 H, H-14), 2.1 (ddq, $^2J_{Hb-Ha}$=15.5 Hz, $^3J_{Hb-CH}$=7 Hz, $^5J_{Hb-CF3}$=1 Hz 1 H, Hb), 3.0 (ddq, $^2J_{Ha-Hb}$=15.5 Hz, $^3J_{Ha-CH}$=7 Hz, $^5J_{Hb-CF3}$=1 Hz, 1 H, Ha), 3.5 (m $^3J_{CH-Ha}$=$^3J_{CH-Hb}$=6.5 Hz, 1 H), 5.7 (s, 1 H, H-12), 8.8 (s br, 2 H, COOH).

$^{13}$C δ (ppm) 19.8 (C-15), 24.2 (C-16), 25.3 (C-14), 28.7 (C-8), 33.8 (C-7), 35.8 (C-4), 37.5 (C-6), 45.3 (C-8a), 50.1 (C-17), 51.2 (C-5a), 77.5 (C-12a), 90.5 (C-12), 105 (C-3), 112 (C-9), 120.1 (q, $^1J$=278, CF$_3$), 137.5 (q, $^2J$=34.5, C-10), 173 (CO), 173.1 (CO), 120.1 (CF$_3$).

Substitution by ethanethiol

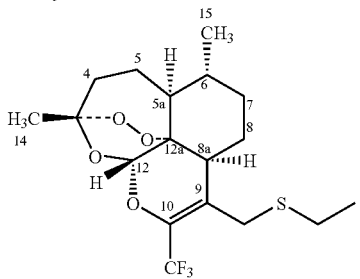

Ethanethiol (0.02 ml, 1.2 eq, 0.3 mmol) and NaH (1.2 eq, 12 mg) are placed, under argon in 10 ml of THF. Allylic bromide (100 mg, 1 eq, 0.24 mmol) is added to the mixture. The reaction medium is agitated for 1 hour 30 minutes at ambient temperature then hydrolysed with a NaCl saturated solution. The aqueous phase is extracted with Et$_2$O then the organic phase is dried over MgSO$_4$. After evaporation of the solvent, the compound is purified by silica gel chromatography (EP/AcOEt: 95/5) in order to produce a colourless oil (30 mg) with a yield of 31%.

$^{19}$F δ (ppm) −64.14 ppm (s, 3 F, CF$_3$)

$^1$H δ (ppm) 0.99 (d, $^3J_{H15-H6}$=6.5 Hz, 3H, CH$_3$-15), 1.1 (m, 1 H, H-7), 1.22 (t, $^3J_{CH3-CH2}$=7.3 Hz, 3 H, CH$_3$), 1.3 (m, 1 H, H-8), 1.41 (s, 3 H, CH$_3$-14), 1.5 (m, 1 H, H-6), 1.55 (m, 1 H, H-5a), 1.7 (dq, $^2J$=13 Hz, $^3J_{H7'-H8}$=$^3J_{H7'-H8'}$=$^3J_{H7'H6}$=3 Hz, 1 H, H-7'), 1.95 (m, 1 H, H-5'), 2.0 (m, 1 H, H-8'), 2.05 (m, 1 H, H-4'), 2.4 (m, 1 H, H-4), 2.49 (q, $^3J_{CH2-CH3}$=7 Hz, 2 H, CH$_2$), 2.53 (dd, $^3J_{H8a-H8}$=7 Hz, $^3J_{H8a-H8}$=5 Hz, 1 H, H-8a), 2.98 (dq, $^2J$=14.5 Hz, $^5J_{Ha-CF3}$=2 Hz, 1 H, Ha), 3.74 (dq, $^2J$=14.5 Hz, $^5J_{Hb-CF3}$=1 Hz, 1 H, Hb), 5.7 (s, 1 H, H-12).

$^{13}$C δ (ppm) 14.2 (CH$_3$), 20.0 (C-15), 24.2 (C-5), 24.3 (CH$_2$), 25.5 (C-14), 28.7 (C-8), 29.12 (q, J=3 Hz, CH$_2$—S), 33.9 (C-7), 35.9 (C-4), 37.5 (C-6), 42.5 (C-8a), 50.2 (C-5a), 77.6 (C-12a), 90.8 (C-12), 104.9 (C$_3$), 112.5 (J=2 Hz, C-9), 120.5 (q, J=275 Hz, CF$_3$), 136.9 (q, J=34 Hz, C-10).

[α]$^{33}_D$=+33.6° (c=1.1, MeOH)

II Compounds of Formulae (Ib) and (Ic)

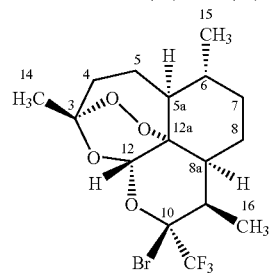

The C-10 brominated starting compound is described in *Organic Letters* 2002, 4 (5), 757-759.

RMN (CDCl$_3$): δ (ppm)

$^1$H 0.98 (qd, $^2J_{H7ax-H7eq}$=$^3J_{H7ax-H8ax}$=$^3J_{H7ax-H6}$=13.5 Hz, $^3J_{H7ax-H8eq}$=3.5 Hz, 1H, H-7ax), 1.0 (d, $^3J_{H15-H6}$=6 Hz, 3H, CH$_3$-15), 1.15 (d, $^3J_{H16-H9}$=7 Hz, 3H, CH$_3$-16), 1.35 (td, $^3J_{H5a-H5ax}$=$^3J_{H5a-H6}$=11 Hz, $^3J_{H5a-H5eq}$=6.5 Hz, 1H, H-5a), 1.42 (m, 1H, H-6), 1.43 (s, 3H, CH$_3$-14), 1.55 (tdd, $^2J_{H5ax-H5eq}$=$^3J_{H5a-H4ax}$=13.5 Hz, $^3J_{H5ax-H4eq}$=5 Hz, $^3J_{H5ax-H5a}$=11 Hz, 1H, H-5ax), 1.68 (td, $^3J_{H8a-H9}$=$^3J_{H8a-H8eq}$=4.5 Hz, J$_{H8a-H8ax}$=14 Hz, 1H, H-8a), 1.78 (dq, $^2J_{H7eq-H7ax}$=13 Hz, $^3J_{H7eq-H8ax}$=$^3J_{H7eq-H8eq}$=$^3J_{H7eq-H6}$=3.5 Hz, 1H, H-7eq), 1.86 (dq, $^2J_{H8eq-H8ax}$=14 Hz, J$_{H8eq-H7ax}$=$^3J_{H8eq-H7eq}$=$^3J_{H8eq-H8a}$=3.5 Hz, 1H, H-8eq), 1.95 (dddd, $^2J_{H5eq-H5ax}$=14 Hz, $^3J_{H5eq-H5a}$=6 Hz, $^3J_{H5eq-H4ax}$=4 Hz, $^3J_{H5eq-H4eq}$=3 Hz, 1H, H-5eq), 2.1 (ddd, $^2J_{H4eq-H4ax}$=14.5 Hz, $^3J_{H4eq-H5ax}$=5 Hz, $^3J_{H4eq-H5eq}$=3 Hz, 1H, H-4eq), 2.29 (qd, $^2J_{H8ax-H8eq}$=$^3J_{H8ax-H7ax}$=$^3J_{H8ax-H8a}$=14 Hz, $^3J_{H8ax-H7eq}$=3.5 Hz, 1H, H-8ax), 2.4 (td, $^2J_{H4ax-H4eq}$=$^3J_{H4ax-H5ax}$=14 Hz, $^3J_{H4ax-H5eq}$=4 Hz, 1H, H-4ax), 2.95 (qd, $^3J_{H9-H16}$=7 Hz, $^3J_{H9-H8a}$=5.5 Hz, 1H, H-9), 5.55 (s, 1H, H-12)

$^{13}$C 15.6 (C-16), 20.5 (C-15), 23 (C-8), 25 (C-5), 26 (C-14), 33.2 (C-9), 34.9 (C-7), 36.2 (C-4), 37.8 (C-6), 47 (C-8a), 52.7 (C-5a), 80 (C-12 a), 92 (C-12), 101 (C-10), 106 (C-3), CF$_3$ not observed.

$^{19}$F −77.9 (s, 3 F, CF$_3$)

| Elementary analysis for C$_{16}$H$_{22}$F$_3$O$_4$ (415.25 g. mol$^{-1}$) | | |
|---|---|---|
| % Calculated | C 46.30% | H 5.34% |
| % Found | C 46.24% | H 5.37% |

T$_{Melting}$=116° C.

[α]$_D$=+182 (0.9; MeOH)

General Operating Mode:

The C-10 brominated compound (415 mg; 1 mmol) is dissolved in dichloromethane (5 mL). Hexafluoroisopropanol (520 µL; 5 mmol) and then the nucleophile (10 mmol) are added to this solution. The reaction mixture is treated with an aqueous solution of sodium bicarbonate after 12 hours agitation at room temperature, it is dried over magnesium sulphate, and the solvent is evaporated. The product is then obtained by silica gel purification.

Substitution by methanol

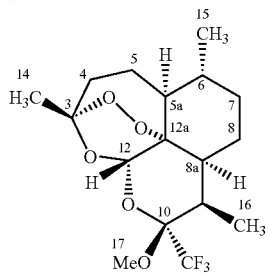

This compound is synthesised according to the general operating mode. After purification on silica gel (petrol ether/ethyl acetate 9/1) 238 mg (65%) of white crystals are obtained.

RAM (CDCl$_3$): δ (ppm)

$^1$H 0.92 (1H$_7$); 0.95 (3H$_{15}$; d; J$_{15-6}$=6.2 Hz); 0.98 (3H$_{16}$; dq; J$_{16-9}$=7.2 Hz; J$_{16-F}$=1.2 Hz); 1.25 (1H$_{5a}$); 1.3 (2H$_6$); 1.42 (3H$_{14}$; s); 1.5 (1H$_{8a}$); 1.5 (1H$_5$); 1.65 (H$_7$); 1.65 (1H$_8$); 1.78 (1H$_8$); 1.9 (H$_5$); 2.03 (H$_{4eq}$; ddd; J$_{4eq-4ax}$=14.6 Hz; J$_{4eq-5ax}$=3.0 Hz; J$_{4eq-5eq}$=5.1 Hz); 2.37 (H$_{4ax}$; ddd; J$_{4ax-4eq}$=14.6 Hz; J$_{4ax-5a}$=13.4 Hz; J$_{4ax-5eq}$=4.1 Hz); 2.83 (H$_9$; dq; J$_{9-16}$=7.2 Hz; J$_{9-8a}$=4.9); 3.43 (3H$_{17}$; q; J$_{17-CF3}$=1.8 Hz); 5.3 (H$_{12}$, s)

$^{13}$C 11.9 (C$_{16}$); 20.0 (C$_{15}$); 23.4 (C$_8$); 24.6 (C$_5$); 25.6 (C$_{14}$); 29.5 (C$_9$); 34.5 (C$_7$); 36.1 (C$_4$); 37.4 (C$_6$); 46.0 (C$_{8a}$); 49.9 (C$_{17}$); 52.0 (C$_{5a}$); 79.8 (C$_{12a}$); 89.1 (C$_{12}$); 98.6 (C$_{10}$; q; $^2$J$_{C-F}$=29 Hz); 104.3 (C$_3$); 122.5 (CF$_3$; q; $^1$J$_{C-F}$=293 Hz)

$^{19}$F −75.5 (s, 3 F, CF$_3$)

| Elementary analysis for C$_{17}$H$_{25}$F$_3$O$_5$ (366.38 g. mol$^{-1}$) | | |
|---|---|---|
| % Calculated | C 55.73% | H 6.88% |
| % Found | C 55.62% | H 6.79% |

T$_{Melting}$=82° C.
[α]$_D$=+135.6 (0.45; MeOH)
Substitution by ethanol

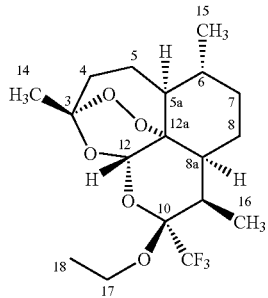

This compound is synthesised according to the general operating mode. After purification on silica gel (petrol ether/ethyl acetate 9/1) 266 mg (70%) of white crystals are obtained.

RMN (CDCl$_3$): δ (ppm)

$^1$H 0.91 (3H$_{15}$; d; J$_{15-6}$=5.5 Hz); 0.96 (3H$_{16}$; d; J$_{16-9}$=7.0 Hz); 1.15 (3H$_{18}$; t; J$_{18-17}$=7.1 Hz); 1.35 (3H$_{14}$; s); 2.31 (1H$_4$; m); 2.76 (H$_9$; m); 3.61 (1H$_{17}$; m); 3.84 (1H$_{17}$; m); 5.27 (1H$_{12}$; s)

$^{13}$C 11.9 (C$_{16}$); 15.1 (C$_{18}$); 19.9 (C$_{15}$); 23.3 (C$_8$); 24.5 (C$_5$); 25.5 (C$_{14}$); 29.5 (C$_9$); 34.5 (C$_7$); 36.0 (C$_4$); 37.4 (C$_6$); 46.0 (C$_{8a}$); 50.0 (C$_{5a}$); 58.2 (C$_{17}$); 79.8 (C$_{12a}$); 89.0 (C$_{12}$); 98.4 (C$_{10}$; q; $^2$J$_{C-F}$=29 Hz); 104.2 (C$_3$); 122.4 (CF$_3$; q; $^1$J$_{C-F}$=293 Hz)

$^{19}$F −75.7 (s, 3 F, CF$_3$)

| Elementary analysis for C$_{18}$H$_{27}$F$_3$O$_5$ (380.41 g. mol$^{-1}$) | | |
|---|---|---|
| % Calculated | C 56.83% | H 7.15% |
| % Found | C 56.72% | H 7.23% |

T$_{Melting}$=94° C.
[α]$_D$=+106.7 (0.52; MeOH)
Substitution by trifluoroethanol

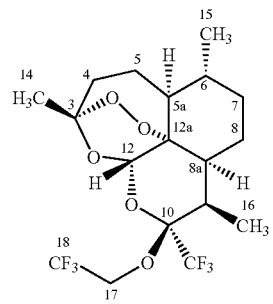

The C-10 brominated compound (1.3 g; 3.1 mmol) is dissolved in trifluoroethanol (5 mL), then triethylamine (316 mg; 3.1 mmol) is added to this solution. The reaction mixture is diluted in ether after 12 hours agitation at room temperature, then the organic phase is washed with an aqueous solution of sodium bicarbonate, dried over magnesium sulphate, and the solvent is evaporated. After silica gel purification (petrol ether/ethyl acetate 95/5) 458 mg (34%) of white crystals are obtained.

RMN (CDCl$_3$): δ (ppm)

$^1$H 0.90 (1H$_{7ax}$); 0.96 (3H$_{15}$; d; J$_{15-6}$=5.9 Hz); 1.04 (3H$_{16}$; dq; J$_{16-9}$=7.2 Hz; J$_{16-CF3}$=0.9 Hz); 1.30 (1H$_6$); 1.40 (1H$_5$); 1.42 (3H$_{14}$; s); 1.55 (1H$_{8a}$); 1.63 (H$_8$); 1.69 (1H$_{7eq}$; dq; J$_{7eq-7ax}$=12.9; J$_{7eq-6}$=J$_{7eq-8ax}$=J$_{7eq-8eq}$=3.4 Hz); 1.82 (1H$_8$); 1.90 (H$_5$); 2.04 (1H$_{4eq}$; ddd; J$_{4eq-4ax}$=14.6 Hz; J$_{4eq-5ax}$=4.5 Hz; J$_{4eq-5eq}$=5.0 Hz); 2.38 (1H$_{4ax}$; ddd; J$_{4ax-4eq}$=14.6 Hz; J$_{4ax-5ax}$=13.6 Hz; J$_{4ax-5eq}$=4.0 Hz); 2.92 (1H$_9$; m); 3.90 (1H$_{17}$; qd; J$_{17-CF3}$=8.5 Hz; J$_{17-17}$=8.5 Hz); 4.35 (1H$_{17}$; qd; J$_{17-CF3}$=8.5 Hz; J$_{17-17}$=8.5 Hz); 5.4 (1H$_{12}$, s)

$^{13}$C 12.0 (C$_{16}$); 20.2 (C$_{15}$); 22.9 (C$_8$); 24.7 (C$_5$); 25.7 (C$_{14}$); 29.3 (C$_9$); 34.7 (C$_7$); 36.2 (C$_4$); 37.6 (C$_6$); 45.7 (C$_{8a}$); 52.1 (C$_{5a}$); 60.3 (C$_{17}$; q; $^1$J$_{C-F}$=36 Hz); 79.9 (C$_{12a}$); 89.4 (C$_{12}$); 99.0 (C$_{10}$; q; $^2$J$_{C-F}$=30 Hz); 104.8 (C$_3$); (CF$_3$; q; $^1$J$_{C-F}$=291 Hz); (CF$_3$; q; $^1$J$_{C-F}$=277 Hz)

$^{19}$F −74.3 (3F; t; $^1$J$_{F-H}$=8.5 Hz); −75.9 (s, 3 F, CF$_3$)

| Elementary analysis for C$_{18}$H$_{24}$F$_6$O$_5$ (434.38 g. mol$^{-1}$) | | |
|---|---|---|
| % Calculated | C 49.77% | H 5.57% |
| % Found | C 49.81% | H 5.61% |

$T_{Melting}=104°$ C.
$[α]_D=+97.5$ (0.44; MeOH)
Substitution by ethylene glycol

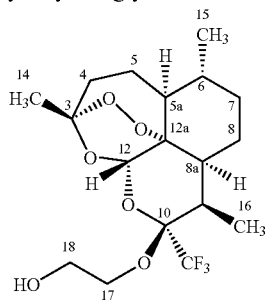

The C-10 brominated compound (1.939 g; 4.7 mmol) is dissolved in a 1/1 mixture of THF and ethylene glycol (8 mL), then triethylamine (472 mg; 4.7 mmol) is added to this solution. The reaction mixture is diluted by ether after 12 hours agitation at room temperature, then the organic phase is washed with an aqueous solution of sodium chloride, dried over magnesium sulphate, and the solvent is evaporated. After silica gel purification (petrol ether/ethyl acetate 9/1) 637 mg (37%) of pale yellow crystals are obtained.

RMN (CDCl$_3$): δ (ppm)
$^1$H 0.95 (3H$_{15}$; d; $J_{15-6}=5.8$ Hz); 1.01 (3H$_{16}$; d; $J_{16-9}=7.3$ Hz); 1.42 (3H$_{14}$; s); 2.37 (1H$_4$; m); 2.86 (H$_9$; m); 3.75 (3H; m); 3.98 (1H); 5.5 (H$_{12}$)
$^{13}$C 12.0 (C$_{16}$); 20.1 (C$_{15}$); 23.1 (C$_8$); 24.6 (C$_5$); 25.6 (C$_{14}$); 29.6 (C$_9$); 34.6 (C$_7$); 36.2 (C$_4$); 37.3 (C$_6$); 46.0 (C$_{8a}$); 52.1 (C$_{5a}$); 61.6 (C$_{17\ ou\ 18}$); 64.4 (C$_{17\ ou\ 18}$); 80.1 (C$_{12a}$); 89.1 (C$_{12}$); 98.6 (C$_{10}$; q; $^2J_{C-F}=29$ Hz); 104.4 (C$_3$); 122.5 (CF$_3$; q; $^1J_{C-F}=293$ Hz)
$^{19}$F −76.0 (s, 3 F. CF$_3$)

| Elementary analysis for C$_{18}$H$_{27}$F$_3$O$_6$ (396.41 g. mol$^{-1}$) | | |
|---|---|---|
| % Calculated | C 54.54% | H 6.87% |
| % Found | C 54.51 | H 6.87 |

$T_{Melting}=92°$ C.
$[α]_D=+109.6$ (0.44; MeOH)
Substitution by acetonitrile

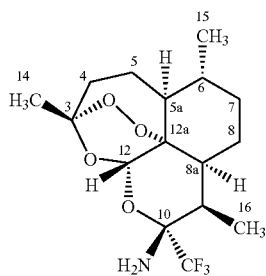

The C-10 brominated compound (538 g; 1.3 mmol) is dissolved in acetonitrile (10 mL), then succinic acid (3 g; 26 mmol) and triethylamine (655 mg; 6.5 mmol) are added to this solution. After two days agitation at room temperature, the reaction mixture is diluted with ethyl acetate and the organic phase is washed with an aqueous solution of sodium chloride, it is dried over magnesium sulphate, and the solvent is evaporated. After silica gel purification (petrol ether/ethyl acetate 5/5) 114 mg (25%) of white crystals are obtained.

RMN (CDCl$_3$): δ (ppm)
$^1$H 0.89 (3H15; d; $J_{15-6}=4.3$ Hz); 1.02 (3H16; d; J16-9=7.4 Hz); 1.34 (3H14; s); 2.93 (H9; m); 5.37 (NH; s large); 5.69 (H12; s broad)
$^{13}$C 12.3 (C$_{16}$); 19-9 (C$_{15}$); 22.9 (C$_8$); 24.4 (C$_5$); 25.5 (C$_{14}$); 29.6 (C$_9$); 34.3 (C$_7$); 36.0 (C$_4$); 37.2 (C$_6$); 45.9 (C$_{8a}$); 51.9 (C$_{5a}$); 79.4 (C$_{12a}$); 89.2 (C$_{12}$); 98.6 (C$_{10}$; q; $^2J_{C-F}=29$ Hz); 104.5 (C$_3$); 123.1 (CF$_3$; q; $^1J_{C-F}=$Hz)
$^{19}$F −79.6 (s, 3 F, CF$_3$)

| Elementary analysis for C$_{16}$H$_{24}$F$_3$NO$_4$ (351.37 g. mol$^{-1}$) | | | |
|---|---|---|---|
| % Calculated | C 54.69% | H 6.88% | N 3.99% |
| % Found | C 53.30% | H 6.52% | N 3.02% |

$T_{Melting}=145°$ C.
$[α]_D=+134.8$ (0.18; MeOH)
Substitution by succinic acid

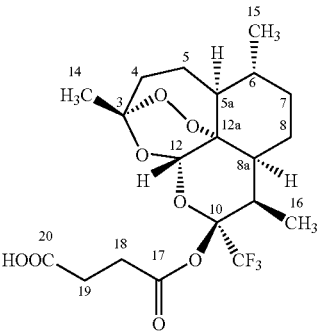

The C-10 brominated compound (456 g; 1.1 mmol) is dissolved in a 1/1 mixture of dichloromethane and hexafluoroisopropanol (8 mL), then succinic acid (1.3 g; 11 mmol) and triethylamine (555 mg; 5.5 mmol) are added to this solution. After 12 hours agitation at room temperature, the reaction mixture is diluted with ethyl acetate, then the organic phase is washed with an aqueous solution of sodium chloride, drying is performed over magnesium sulphate, and solvent is evaporated. After silica gel purification (petrol ether/ethyle acetate 8/2 then AcOEt alone) 328 mg (66%) of a beige foam is obtained.

RMN (CDCl$_3$): δ (ppm)
$^1$H 0.94 (3H15; d; J15-6=5.5 Hz); 1.05 (3H16; d; J16-9=6.9 Hz); 1.40 (3H14; s); 2.34 (1H4; m); 2.62 (2H18 et 2H19; m); 2.88 (H9; m); 5.54 (H12; s); 8.39 (COOH; s broad)
$^{13}$C 11.95 (C$_{16}$); 20.0 (C$_{15}$); 23.0 (C$_8$); 24.3 (C$_5$); 25.5 (C$_{14}$); 28.5 (C$_{18}$; m); 29.9 (C$_{19}$); 30.1 (C$_9$); 34.4 (C$_7$); 36.0 (C$_4$); 37.1 (C$_6$); 45.6 (C$_{8a}$); 51.8 (C$_{5a}$); 79.5 (C$_{12a}$); 90.4 (C$_{12}$); 102.1 (C$_{10}$; q; $^2J_{C-F}=32$ Hz); 104.7 (C$_3$); 121.5 (CF$_3$; q; $^1J_{C-F}=289$ Hz); 168.5 (C$_{17}$); 177.4 (C$_{20}$)
$^{19}$F −77.2 (s, 3 F, CF$_3$)

| Elementary analysis for C$_{20}$H$_{27}$F$_3$O$_8$ (452.43 g. mol$^{-1}$) | | |
|---|---|---|
| % Calculated | C 53.10% | H 6.02% |
| % Found | C 52.49% | H 6.04% |

Substitution by anisidine

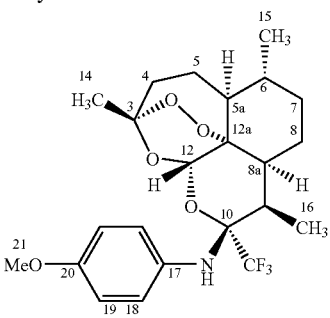

This compound is synthesised according to the general operating mode. After silica gel purification (petrol ether/ethyl acetate 9/1) 114 mg (25%) of an orange foam is obtained.

RMN (CDCl$_3$): δ (ppm)

$^1$H 0.95 (3H15; d; J15-6=5.4 Hz); 1.11 (3H16; d; J16-9=7.3 Hz); 1.47 (3H14; s); 2.39 (1H4; m); 3.05 (H9; m); 3.63 (NH; s broad); 3.75 (3H21; s); 5.56 (H12; s); 6.81 (2H$_{Ar}$; m); 7.04 (2H$_{Ar}$; m)

$^{13}$C 12.6 (C$_{16}$); 20.0 (C$_{15}$); 23.5 (C$_8$); 24.5 (C$_5$); 25.7 (C$_{14}$); 30.1 (C$_9$); 34.3 (C$_7$); 36.2 (C$_4$); 37.2 (C$_6$); 46.3 (C$_{8a}$); 52.2 (C$_{5a}$); 55.2 (C$_{21}$); 80.1 (C$_{12a}$); 88.3 (C$_{10}$; q; $^2$J$_{C-F}$=28 Hz); 90.0 (C$_{12}$); 104.3 (C$_3$); 114.2 (C$_{18}$); 119.2 (C$_{19}$); 123.8 (CF$_3$; q; $^1$J$_{C-F}$=294 Hz); 136.4 (C$_{17}$); 154.0 (C$_{20}$)

$^{19}$F −75.5 (s, 3 F, CF$_3$)

| Elementary analysis for C$_{23}$H$_{30}$F$_3$NO$_5$ (457.49 g. mol$^{-1}$) | | | |
|---|---|---|---|
| % Calculated | C 60.38% | H 6.61% | N 3.06% |
| % Found | C 60.22% | H 6.65% | N 2.97% |

[α]$_D$=+93.6 (0.34; MeOH)

Substitution by allylic alcohol

This compound is synthesised according to the general operating mode. After silica gel purification (petrol ether/acetate d'éthyle 9/1) 255 mg (65%) of a light yellow oil is obtained.

RMN (CDCl$_3$: δ (ppm)

$^1$H 0.94 (3H$_{15}$; d; J$_{15-6}$=5.8 Hz); 1.01 (3H$_{16}$; dq; J$_{16-9}$=7.2 Hz; $^5$J$_{H-F}$=1.3 Hz); 1.41 (3H$_{14}$; s); 2.37 (1H$_4$; m); 2.85 (H$_9$); 4.15 (1H$_{17}$; dm; J$_{17-17}$=12.8 Hz); 4.35 (1H$_{17}$; dd; J$_{17-17}$=12.8 Hz; J$_{17-18}$=5.8 Hz); 5.15 (1H$_{19}$; dq; J$_{19-18}$=10.3 Hz; J$_{19-19}$=J$_{19-17}$=1.6 Hz); 5.28 (1H$_{19}$; dq; J$_{19-18}$=17.3 Hz; J$_{19-19}$=J$_{19-17}$=1.6 Hz); 5.31 (H$_{12}$; s); 5.89 (H$_{18}$; m)

$^{13}$C 12.2 (C$_{16}$); 20.2 (C$_{15}$); 23.5 (C$_8$); 24.7 (C$_5$); 25.8 (C$_{14}$); 29.7 (C$_9$); 34.7 (C$_7$); 36.2 (C$_4$); 37.6 (C$_6$); 46.1 (C$_{8a}$); 52.1 (C$_{5a}$); 63.9 (C$_{17}$); 80.1 (C$_{12a}$); 89.3 (C$_{12}$); 98.7 (C$_{10}$; q; $^2$J$_{C-F}$=29 Hz); 104.5 (C$_3$); 116.6 (C$_{19}$); 122.6 (CF$_3$; q; $^1$J$_{C-F}$=293 Hz); 134.0 (C$_{18}$)

$^{19}$F −75.9 (s, 3 F, CF$_3$)

| Elementary analysis for C$_{19}$H$_{27}$F$_3$O$_5$ (392.42 g. mol$^{-1}$) | | |
|---|---|---|
| % Calculated | C 58.16% | H 6.94% |
| % Found | C % | H % |

Fluoride elimination

The C-10 compound (1.223 g; 2.9 mmol) is dissolved in anhydrous THF (20 mL), then methyl-lithium (3.7 mL; 1.6M; 5.9 mmol) is added at −78° C. under argon. After 2 hours at low temperature agitation is performed 1 more hour at room temperature, then hydrolysis is performed with a saturated ammonium chloride solution. After silica gel purification (petrol ether/ethyle-acetate 9/1) 575 mg (62%) of a pale yellow oil is obtained.

RMN (CDCl$_3$): δ (ppm)

$^1$H 0.93 (3H$_{15}$; dm; J$_{15-6}$=5.7 Hz); 1.06 (3H$_{16}$; t; J$_{16-9}$=$^4$J$_{H-F}$=7.0 Hz); 1.41 (3H$_{14}$; d; J$_{H-F}$=1.4 Hz); 2.35 (1H$_4$; m); 3.23 (H$_9$; m); 5.3 (H$_{12}$)

$^{13}$C 12.9 (C$_{16}$; d; $^4$J$_{C-F}$=9.4 Hz); 19.9 (C$_{15}$); 21.9 (C$_8$); 24.6 (C$_5$); 25.5 (C$_{14}$); 28.5 (C$_9$; d; $^3$J$_{C-F}$=3.9 Hz); 33.6 (C$_7$); 35.8 (C$_4$); 37.1 (C$_6$); 46.2 (C$_{8a}$; $^4$J$_{C-F}$=2.3 Hz); 51.3 (C$_{5a}$); 80.7 (C$_{12a}$); 93.6 (C$_{12}$; dd; $^4$J$_{C-F}$=2.3 Hz; $^4$J$_{C-F}$=1.1 Hz); 104.4 (C$_3$); 114.5 (C$_{10}$; dd; $^2$J$_{C-F}$=35 Hz; $^2$J$_{C-F}$=14 Hz); 154.9 (CF$_2$; dd; $^1$J$_{C-F}$=286 Hz; $^1$J$_{C-F}$=282 Hz)

$^{19}$F −117.0 (1F; dm; $^1$J$_{F-F}$=80 Hz); −98.9 (1F; dm; $^1$J$_{F-F}$=80 Hz)

| Elementary analysis for C$_{16}$H$_{22}$F$_2$O$_4$ (316.35 g. mol$^{-1}$) | | |
|---|---|---|
| % Calculated | C 60.75% | H 7.01% |
| % Found | C 60.12% | H 7.10% |

Oxidation to acid

The abovementioned allylic compound (595 mg; 1.5 mmol) is dissolved in a tertiary mixture of carbon tetrachloride (3 mL), acetonitrile (3 mL) and water (5 mL). Sodium periodate (1.6 g; 7.6 mmol) and ruthenium trichloride (8 mg; 0.03 mmol) are then added to this solution. After one night the reaction mixture is diluted with ethyl acetate and the organic phase is washed with an aqueous solution of sodium bisulfite. After silica gel purification (petrol ether/ethyl acetate 7/3) 299 mg (48%) of a colourless foam is obtained.

RMN (CDCl$_3$): δ (ppm)

$^1$H 0.91 (3H$_{15}$; d; J$_{15-6}$=5.7 Hz); 1.00 (3H$_{16}$; d; J$_{16-9}$=7.1 Hz); 1.37 (3H$_{14}$; s); 2.30 (1H$_4$; m); 2.84 (H$_9$; m); 4.18 (1H$_{17}$; d; J$_{17-17}$=16.4 Hz); 4.62 (1H$_{17}$; d; J$_{17-17}$=16.4 Hz); 5.44 (H$_{12}$; s); 8.55 (COOH broad)

$^{13}$C 12.1 (C$_{16}$); 20.2 (C$_{15}$); 22.8 (C$_8$); 24.7 (C$_5$); 25.7 (C$_{14}$); 29.5 (C$_9$); 34.7 (C$_7$); 36.2 (C$_4$); 37.3 (C$_6$); 45.9 (C$_{8a}$); 52.1 (C$_{5a}$); 60.7 (C$_{17}$); 80.2 (C$_{12a}$); 89.6 (C$_{12}$); 98.9 (C$_{10}$; q; $^2$J$_{C-F}$=29 Hz); 104.7 (C$_3$); 122.4 (CF$_3$; q; $^1$J$_{C-F}$=292 Hz); 175.5 (C$_{18}$)

$^{19}$F −76.1 (s, 3 F, CF$_3$)

| Elementary analysis for C$_{18}$H$_{25}$F$_3$O$_7$ (410.39 g. mol$^{-1}$) | | |
|---|---|---|
| % Calculated | C 52.68% | H 6.14% |
| % Found | C 52.75% | H 6.31% |

[α]$_D$=+71.2 (0.80; MeOH)
IR: ν (cm$^{-1}$) 1728 (CO); 3200 broad (COOH)
Oxidation to aldehyde

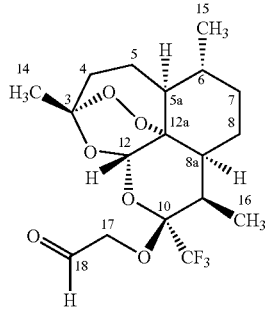

This compound is obtained as an intermediate product of the latter reaction. Thus, operating conditions have not been optimised to obtain it as a unique compound.

RMN (CDCl$_3$): δ (ppm)

$^1$H 0.94 (3H$_{15}$; d; J$_{15-6}$=5.5 Hz); 1.04 (3H$_{16}$; d; J$_{16-9}$=7.1 Hz); 1.39 (3H$_{14}$; s); 2.35 (1H$_4$; m); 2.88 (H$_9$; m); 4.35 (1H$_{17}$; dm; J$_{17-17}$=18.4 Hz); 4.54 (1H$_{17}$; d; J$_{17-17}$=18.4 Hz); 5.28 (H$_{12}$; s); 9.6 (H$_{18}$)

$^{13}$C 12.0 (C$_{16}$); 20.1 (C$_{15}$); 23.1 (C$_8$); 24.5 (C$_5$); 25.6 (C$_{14}$); 29.4 (C$_9$); 34.5 (C$_7$); 36.0 (C$_4$); 37.3 (C$_6$); 45.6 (C$_{8a}$); 51.8 (C$_{5a}$); 68.4 (C$_{17}$); 79.9 (C$_{12a}$); 89.4 (C$_{12}$); 98.8 (C$_{10}$; q; $^2$J$_{C-F}$=29 Hz); 104.6 (C$_3$); 122.2 (CF$_3$; q; $^1$J$_{C-F}$=292 Hz); 197.8 (C$_{18}$)

$^{19}$F −76.3 (s, 3 F, CF$_3$)

| Elementary analysis for C$_{18}$H$_{25}$F$_3$O$_6$ (394.39 g. mol$^{-1}$) | | |
|---|---|---|
| % Calculated | C 54.82% | H 6.39% |
| % Found | C 54.71% | H 6.47% |

[α]$_D$=+94.0 (0.32; MeOH)
Substitution by HPU (Hydrogen Peroxide Urea)

The C-10 brominated compound (92 mg; 0.22 mmol) is dissolved in dichloromethane (2 mL). A solution of the hydrogen peroxide-urea complex (208 mg; 2.2 mmol) is then added to it in hexafluoroisopropanol (2 mL). After 12 hours agitation at room temperature excess HPU is precipitated by adding diethylic ether, then filtration over silica is performed. The solvent is then cautiously evaporated. After silica gel purification (petrol ether/ethyl acetate 9/1) 59 mg (73%) of white crystals is obtained.

RMN (CDCl$_3$): δ (ppm)

$^1$H 0.90 (3H$_{15}$; d; J$_{15-6}$=Hz); 0.94 (3H$_{16}$; d; J$_{16-9}$=8.0 Hz); 1.38 (3H$_{14}$; s); 2.32 (1H$_4$; m); 2.95 (H$_9$; m); 5.53 (H$_{12}$; S); 8.83 (OH; s)

$^{13}$C 11.6 (C$_{16}$); 20.0 (C$_{15}$); 24.0 (C$_8$); 24.6 (C$_5$); 25.6 (C$_{14}$); 30.1 (C$_9$); 34.3 (C$_7$); 36.1 (C$_4$); 37.4 (C$_6$); 45.4 (C$_{8a}$); 51.9 (C$_{5a}$); 79.9 (C$_{12a}$); 89.7 (C$_{12}$); (C$_{10}$; q; $^2$J$_{C-F}$=Hz); 105.0 (C$_3$); 116.6 (C$_{19}$); 121.6 (CF$_3$; q; $^1$J$_{C-F}$=290 Hz)

$^{19}$F −74.6 (s, 3 F, CF$_3$)

| Elementary analysis for C$_{16}$H$_{23}$F$_3$O$_6$ (368.35 g. mol$^{-1}$) | | |
|---|---|---|
| % Calculated | C 52.17% | H 6.29% |
| % Found | C 51.28% | H 6.66% |

Oxidation to diol

The abovementioned allylic compound (396 mg; 11.0 mmol) is dissolved in a terbutanol (20 mL) water (2 mL) mixture. N-oxide morpholine (150 mg; 1.1 mmol) and osmium tetraoxide (13 mg; 0.05 mmol) are then added to this solution. After 3 hours, the reaction mixture is diluted with ethyl acetate, then the organic phase is washed successively with a sodium bisulfite aqueous solution, a sodium bicarbonate solution, and a sodium chloride solution. After silica gel purification (petrol ether/ethyl acetate 8/2) 257 mg (60%) of a colourless foam is obtained.

RMN (CDCl$_3$): δ (ppm)

$^1$H 0.94 (3H$_{15}$; d; J$_{15-6}$=5.8 Hz); 1.00 (3H$_{16}$; d; J$_{16-9}$=7.3 Hz); 1.41 (3H$_{14}$; s); 2.37 (1H$_4$; m); 2.86 (1H$_9$); 3.41-4.05 (5H; m); 5.48 (H$_{12\ mino}$); 5.55 (H$_{12\ majo}$)

$^{13}$C 11.7 (C$_{16}$); 19.7 (C$_{15}$); 22.6 (C$_8$); 22.8 (C$_8$); 24.3 (C$_5$); 25.2 (C$_{14}$); 29.3 (C$_5$); 34.4 (C$_7$); 35.8 (C$_4$); 36.85 (C$_6$); 36.90 (C$_6$); 45.6 (C$_{8a}$); 45.7 (C$_{8a}$); 51.8 (C$_{5a}$); 63.3 (C$_{19}$); 63.5 (C$_{19}$); 63.6 (C$_{17}$); 64.2 (C$_{17}$); 70.6 (C$_{18}$); 71.0 (C$_{18}$); 79.7 (C$_{12a}$); 79.8 (C$_{12a}$); 88.7 (C)$_{12}$); 88.8 (C$_{12}$); 98.22 (C$_{10}$; q; $^2$J$_{C-F}$=29 Hz); 98.25 (C$_{10}$; q; $^2$J$_{C-F}$=29 Hz); 104.0 (C$_3$); 122.2 (CF$_3$; q; $^1$J$_{C-F}$=293 Hz)

$^{19}$F −76.1 (40%); −76.2 (60%)

| Elementary analysis for C$_{19}$H$_{29}$F$_3$O$_7$ (426.43 g. mol$^{-1}$) | | |
|---|---|---|
| % Calculated | C 53.52% | H 6.85% |
| % Found | C 53.81% | H 6.58% |

Olefin to diol oxidation

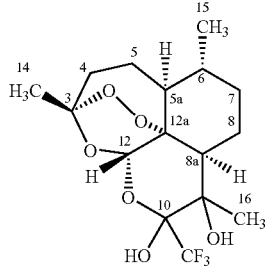

The abovementioned olefin (100 mg; 0.3 mmol) is dissolved in a carbon tetrachloride (1 mL), acetonitrile (1 mL) and water (1.5 mL) mixture. Sodium periodate (1.5 eq) and then ruthenium trichloride (0.02 eq) are added to this solution. After overnight reaction the reaction mixture is diluted with ethyl acetate, then the organic phase is successively washed with a sodium bisulfite aqueous solution, a sodium bicarbonate solution, and a sodium chloride solution. After silica gel purification (petrol ether/ethyl acetate 9/1) 66 mg (65%) of white crystals are obtained (diastereoisomer mixture 65/35).

RMN(CDCl$_3$): δ (ppm)

$^1$H 0.96 (3H$_{15}$; d; J$_{15-6}$=5.9 Hz); 1.00 (H$_{7ax}$); 1.30 (1H$_6$); 1.32 (H$_{5a}$); 1.36 (3H$_{16}$; s); 1.44 (3H$_{14}$; s); 1.50 (1H$_8$); 1.53 (1H$_5$); 1.66 (H$_{7eq}$; dq; J$_{7eq-7ax}$=13.1; J$_{7eq-6}$=J$_{7eq-8ax}$=J$_{7eq-8eq}$=3.3 Hz); 1.76 (H$_{8a}$; dd; J$_{8a-8ax}$=12.0 Hz; J$_{8a-8eq}$=5.7 Hz); 1.90 (1H$_8$); 1.92 (1H$_5$); 2.08 (H$_{4eq}$; ddd; J$_{4eq-4ax}$=14.6 Hz; J$_{4eq-5ax}$=4.8 Hz; J$_{4eq-5eq}$=3.0 Hz); 2.37 (H$_{4ax}$; ddd; J$_{4ax-4eq}$=14.6 Hz; J$_{4ax-5ax}$=13.8 Hz; J$_{4ax-5eq}$=4.2 Hz); 3.21 (OH$_{10}$; s); 4.66 (OH$_9$; s); 5.61 (H$_{12}$, s)

$^{13}$C 20.2 (C$_{15}$); 22.6 (C$_{16}$; q; $^4$J$_{C-F}$=3.1 Hz); 24.5 (C$_8$); 25.5 (C$_5$); 25.6 (C$_{14}$); 34.3 (C$_7$); 36.1 (C$_4$); 37.6 (C$_6$); 52.0 (C$_{5a}$); 52.1 (C$_{8a}$; q; 4J$_{C-F}$=1.6 Hz); 72.1 (C$_9$; q; 3JC-F=1.2 Hz); 83.0 (C$_{12a}$); 88.9 (C$_{12}$); 98.8 (C$_{10}$; q; $^2$J$_{C-F}$=29 Hz); 104.8 (C$_3$); 116.6 (C$_{19}$); 122.5 (CF$_3$; q; $^1$J$_{C-F}$=289 Hz)

$^{19}$F −79.3 (s, 3 F, CF$_3$)

| Elementary analysis for C$_{16}$H$_{23}$F$_3$O$_6$ (368.35 g. mol$^{-1}$) | | |
|---|---|---|
| % Calculated | C 52.17% | H 6.29% |
| % Found | C 52.24% | H 6.36% |

Substitution by dimethanol benzene

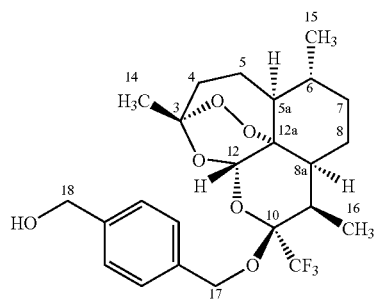

This compound is synthesised according to the general operating mode with monoacetylated dimethanol benzene as a nucleophile. The corresponding ester is then dissolved in methanol (3 mL) and potassium carbonate (2 eq) is added to it. After silica gel purification (petrol ether/ethyl acetate 9/1) 25% of white crystals is obtained.

RMN (CDCl$_3$): δ (ppm)

$^1$H 0.91 (3H$_{15}$; d; J$_{15-6}$=5.9 Hz); 1.05 (3H$_{16}$; d; J$_{16-9}$=7.3 Hz); 1.44 (3H$_{14}$; s); 2.38 (1H$_4$; m); 2.90 (1H$_9$; m); 4.69 (2H$_{18}$; s); 4.72 (1H$_{17}$; d; J$_{17-17}$=11.7 Hz); 4.83 (1H$_{17}$; d; J$_{17-17}$=11.7 Hz); 5.37 (H$_{12}$; s)

$^{13}$C 12.2 (C$_{16}$; m); 20.1 (C$_{15}$); 23.4 (C$_8$); 24.6 (C$_5$); 25.8 (C$_{14}$); 29.7 (C$_9$); 34.5 (C$_7$); 36.2 (C$_4$); 37.5 (C$_6$); 45.9 (C$_{8a}$); 52.0 (C$_{5a}$); 64.7 (C$_{17}$; q; $^4$J$_{C-F}$=2.0 Hz); 65.0 (C$_{18}$); 79.7 (C$_{12a}$); 80.0 (C$_{12a}$); 89.4 (C$_{12}$); 88.8 (C$_{12}$); 98.9 (C$_{10}$; q; $^2$J$_{C-F}$=29 Hz); 104.6 (C$_3$); 122.6 (CF$_3$; q; $^1$J$_{C-F}$=293 Hz); 127.0 (C$_{Ar}$); 127.7 (C$_{Ar}$); 136.9 (C$_{Ar}$); 140.3 (C$_{Ar}$)

$^{19}$F −75.4 (s, 3 F, CF$_3$)

| Elementary analysis for C$_{24}$H$_{31}$F$_3$O$_6$ (472.51 g. mol$^{-1}$) | | |
|---|---|---|
| % Calculated | C 61.01% | H 6.61% |
| % Found | C % | H % |

III Biological Activities

The above products have proved to be active on P. Falciparum, equally well on resistant as non-resistant strains, as well as in vivo in the Peters test on mice infected by Plasmodium berghei.

Thus, by way of an example, the compound substituted by piperazine ethanol has nanomolar IC$_{50}$ values of 17 and of 3 respectively vis-à-vis sensitive and resistant (W2) strains of P. falciparum respectively. The same compound provides the mice with protection, all the mice survive in the Peters test after 20 days with a daily dose of 50 mg/Kg for 4 days.

The dosages used for the compounds of the invention are thus comparable to those used for artemether, or artesunate.

The invention claimed is:

1. A compound of the formula:

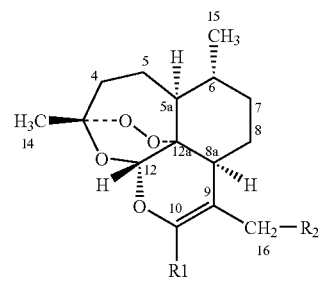

in which:

R₁ is CF₃, and

R₂ is Br or a group that renders said compound water-soluble, said group being derived from piperazine, morpholine, alkylamine, alkoxy, ester or diester, acid or diacid, thioalkyl, alkylhydroxyl, or glycosyl.

2. The compound according to claim 1, in which R₂ is:

derived from paperazine, optionally substituted by an amine, alcohol, or acid function;

a morpholino group of formula,

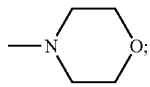

an alkylamine group of 1 to 10 carbon atoms, optionally substituted by a hydrozyl;

an alkoxy group of 1 to 10 carbon atoms, optionally substituted by a hydroxyl or amine function;

an alkyl group of 1 to 10 carbon atoms, substituted by one or more —COOR functions in which R represents H or an alkyl, alkylamine, or alkylhydroxy group of 1 to 4 carbon atoms;

a thioalkyl group of 1 to 6 carbon atoms;

an alkylhydroxyl group of 1 to 10 carbon atoms; or a glycosyl group.

3. The compound according to claim 2, in which R₂ is selected from the group consisting of:

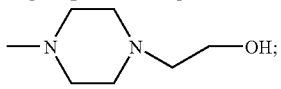

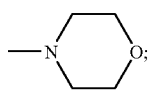

—NH—CH₂—CH₃;

an —NH—CH₂—CH₂—OH group;

—O—CH₂—CH₃;

an —O—CH₂—CH₂—OH group;

an —O—CH₂—CH₂—NHR group in which R is C₁₋₅ alkyl;

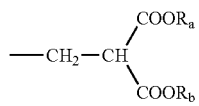

in which $R_a$ and $R_b$ each independent represent H or CH₃;

—S—CH₂—CH₃; and a glucuronic acid or other nonasaccharide group.

4. The compound according to claim 1, said compound being selected from the group consisting of:

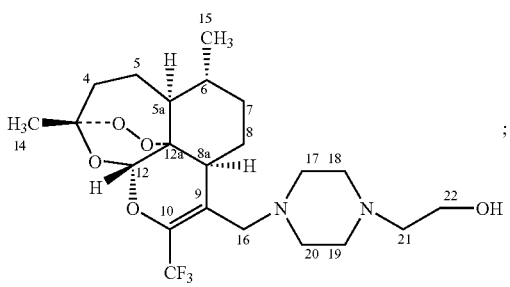

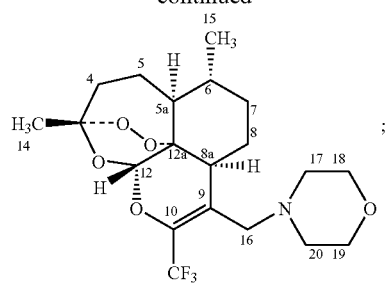

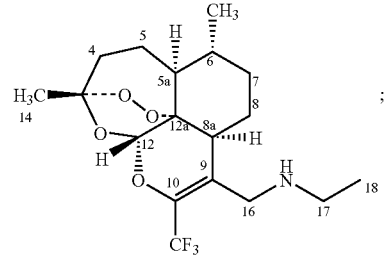

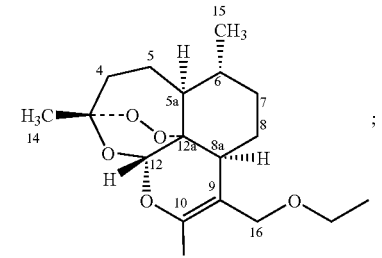

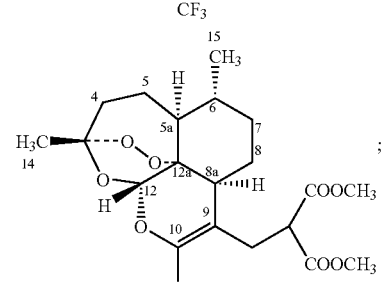

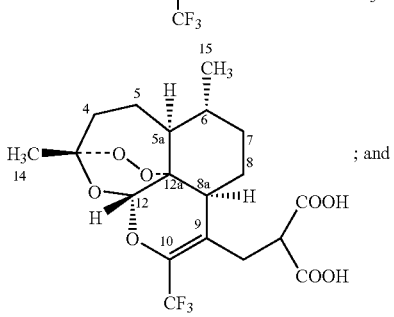

; and

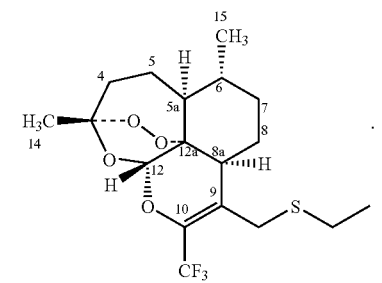

5. A pharmaceutical composition comprising at least one compound according to claim 1, combined with a pharmaceutically acceptable vehicle.

6. The pharmaceutical composition according to claim 5, in a form adapted for administration by oral, injectable, or rectal route.

7. The pharmaceutical composition according to claim 6, in unit dose form permitting administration of said compounds in an amount of 5 mg to 5 g for a dosage of 1 mg/kg/day to 100 mg/kg/day.

8. The pharmaceutical composition according to claim 7, further comprising one or more compounds selected from the group consisting of pyrimethamine, sulfadoxine, quinine, lumefantrine and mefloquine.

9. A composition comprising:
at least one compound according to claim 1,
and at least one other anti-malarial compound.

* * * * *